US010326425B2

(12) United States Patent
Belsick et al.

(10) Patent No.: US 10,326,425 B2
(45) Date of Patent: Jun. 18, 2019

(54) ACOUSTIC RESONATOR WITH REDUCED MECHANICAL CLAMPING OF AN ACTIVE REGION FOR ENHANCED SHEAR MODE RESPONSE

(71) Applicant: Qorvo US, Inc., Greensboro, NC (US)

(72) Inventors: John Belsick, Bend, OR (US); Rick Morton, Bend, OR (US)

(73) Assignee: QORVO US, INC., Greensboro, NC (US)

(*) Notice: Subject to any disclaimer, the term of this patent is extended or adjusted under 35 U.S.C. 154(b) by 215 days.

(21) Appl. No.: 15/357,006

(22) Filed: Nov. 21, 2016

(65) Prior Publication Data

US 2017/0149408 A1 May 25, 2017

Related U.S. Application Data

(60) Provisional application No. 62/257,954, filed on Nov. 20, 2015.

(51) Int. Cl.
*H03H 9/02* (2006.01)
*G01N 29/02* (2006.01)
(Continued)

(52) U.S. Cl.
CPC ....... *H03H 9/02086* (2013.01); *G01N 29/022* (2013.01); *G01N 29/036* (2013.01);
(Continued)

(58) Field of Classification Search
CPC .... G01N 29/022; G01N 29/036; G01N 29/32; G01N 33/5438; G01N 2291/0255;
(Continued)

(56) References Cited

U.S. PATENT DOCUMENTS 4,640,756 A  2/1987  Wang et al.
7,468,608 B2  12/2008  Feucht et al.
(Continued)

OTHER PUBLICATIONS

International Patent Application No. PCT/US2016/063008, filed Nov. 21, 2016; International Search Report / Written Opinion dated Mar. 2, 2017; 10 pages.

(Continued)

*Primary Examiner* — Robert J Pascal
*Assistant Examiner* — Jorge L Salazar, Jr.
(74) *Attorney, Agent, or Firm* — Mueting, Raasch & Gebhardt, P.A.

(57) ABSTRACT

The present disclosure provides an acoustic resonator with reduced mechanical clamping of an active region for enhanced shear mode response. More specifically, the present disclosure provides a solidly mounted BAW resonator device with an active region of piezoelectric material laterally surrounded by an inactive region with a reduced thickness of piezoelectric material such that at least an upper portion of the inactive region along a boundary of the active region is devoid of piezoelectric material. The resonator device provides a discontinuity along opposing lateral edges of the piezoelectric material of the active region to reduce mechanical clamping of the active region in a direction of maximum lateral displacement in shear mode operation. Increasing the mechanical isolation of the active region of piezoelectric material decreases mechanical damping of lateral vibrations of the active region which enhances the shear mode response for quasi-shear mode sensing.

18 Claims, 12 Drawing Sheets

(51) Int. Cl.
H03H 9/17 (2006.01)
G01N 33/543 (2006.01)
G01N 29/036 (2006.01)
G01N 29/32 (2006.01)
H03H 9/13 (2006.01)
H03H 9/15 (2006.01)

(52) U.S. Cl.
CPC ......... *G01N 29/32* (2013.01); *G01N 33/5438* (2013.01); *H03H 9/02015* (2013.01); *H03H 9/13* (2013.01); *H03H 9/172* (2013.01); *H03H 9/175* (2013.01); *G01N 2291/0255* (2013.01); *G01N 2291/0256* (2013.01); *G01N 2291/0422* (2013.01); *G01N 2291/0423* (2013.01); *H03H 2009/155* (2013.01)

(58) Field of Classification Search
CPC ... G01N 2291/0256; G01N 2291/0422; G01N 2291/0423; H03H 9/13; H03H 9/172; H03H 9/175; H03H 2009/155; H03H 9/02669; H03H 9/02; H03H 9/02015; H03H 9/02062; H03H 9/02086
USPC .......................................... 333/186, 187, 188
See application file for complete search history.

(56) References Cited

U.S. PATENT DOCUMENTS

| | | | |
|---|---|---|---|
| 8,409,875 B2 | 4/2013 | Johal et al. | |
| 2002/0190814 A1 | 12/2002 | Yamada et al. | |
| 2005/0148065 A1 | 7/2005 | Zhang et al. | |
| 2006/0125489 A1 | 6/2006 | Feucht et al. | |
| 2008/0247264 A1* | 10/2008 | Gabl .................. | B01F 11/0266 366/127 |

OTHER PUBLICATIONS

Ramakrishnan, et al., "Resonant Frequency Characteristics of a SAW Device Attached to Resonating Micropillars," 2012, Sensors, 12(4):3789-97.

Qorvo US, Inc., "Summary of Sales Activity of Predecessor to Applicant Concerning Tilted Axis Aluminum Nitride Products," Unpublished, Jan. 10, 2017, 1 page.

Bjurström, J. et al., "Design and Fabrication of Temperature Compensated Liquid FBAR Sensors," IEEE Ultrasonics Symposium, Oct. 2-6, 2006, pp. 894-897.

Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.

Mehdizadeh, Emad et al., "Microelectromechanical disk resonators for direct detection of liquid-phase analytes," Sensors and Actuators A: Physical, vol. 216, Sep. 1, 2014, pp. 136-141.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Zhou, Yan et al., "Interfacial Structures and Properties of Organic Materials for Biosensors: An Overview," Sensors, vol. 12, Nov. 6, 2012, pp. 15036-15062.

COMSOL Inc., "Thickness Shear Mode Quartz Oscillator," Solved with COMSOL Multiphysics 5.1, last modified Apr. 7, 2015, 20 pages.

Montero, Julio Mario Dewdney, "Low Loss VHF and UHF Filters for Wireless Communications Based on Piezoelectrically-Transduced Micromechanical Resonators," Dissertation, Department of Electrical Engineering, College of Engineering, University of South Florida, 2012, 210 pages.

* cited by examiner

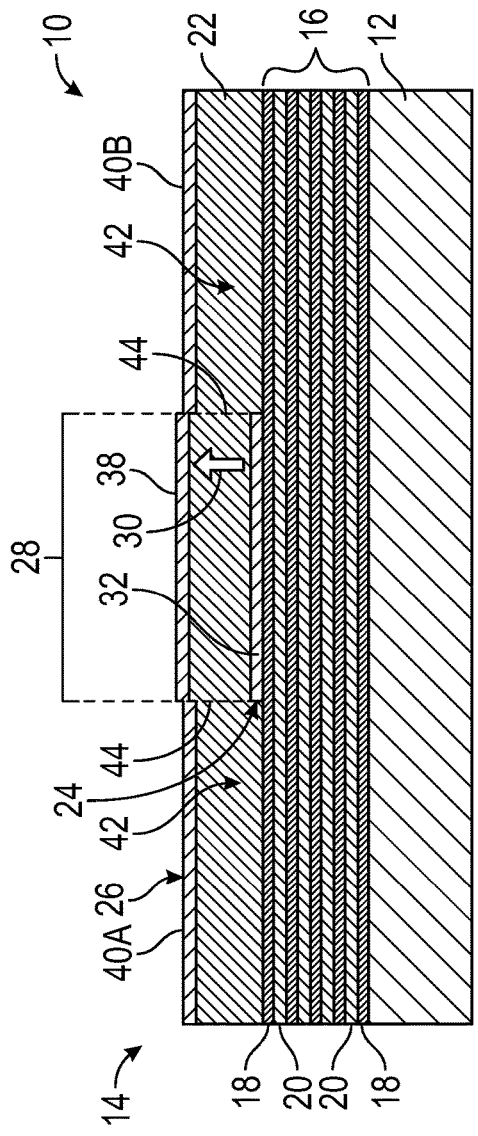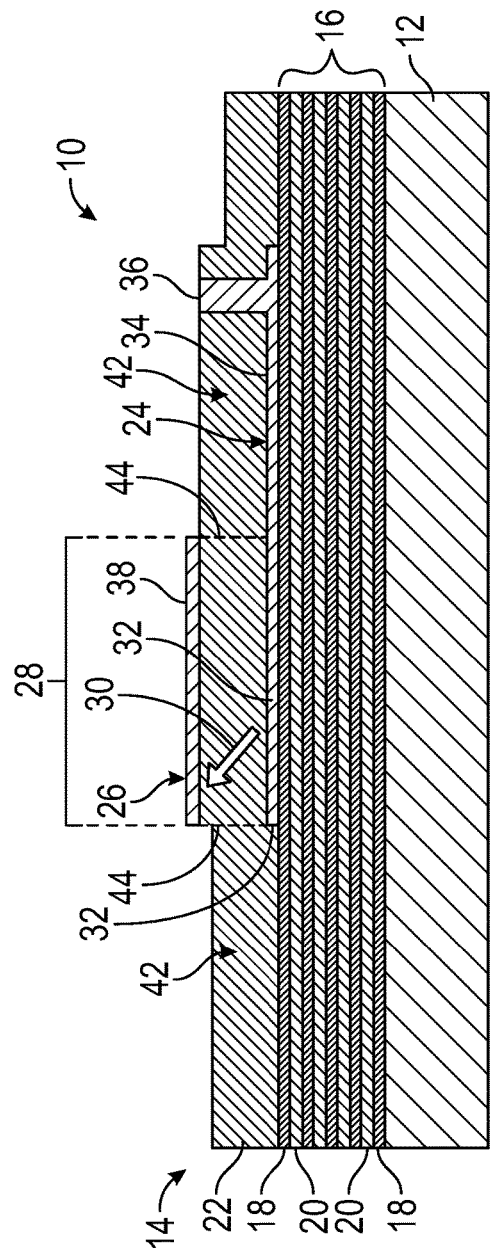
FIG. 1B
FIG. 1C

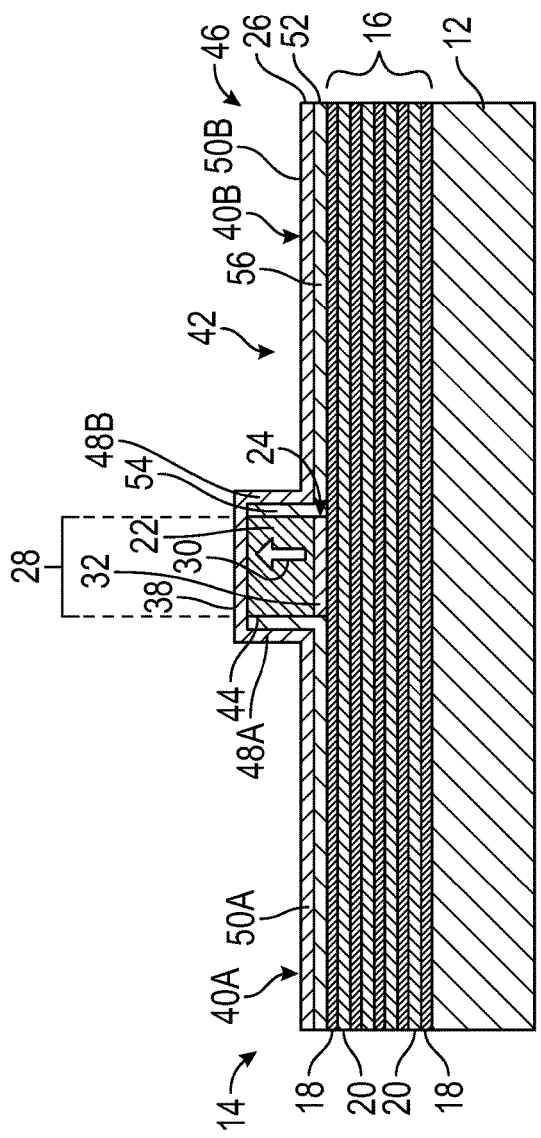
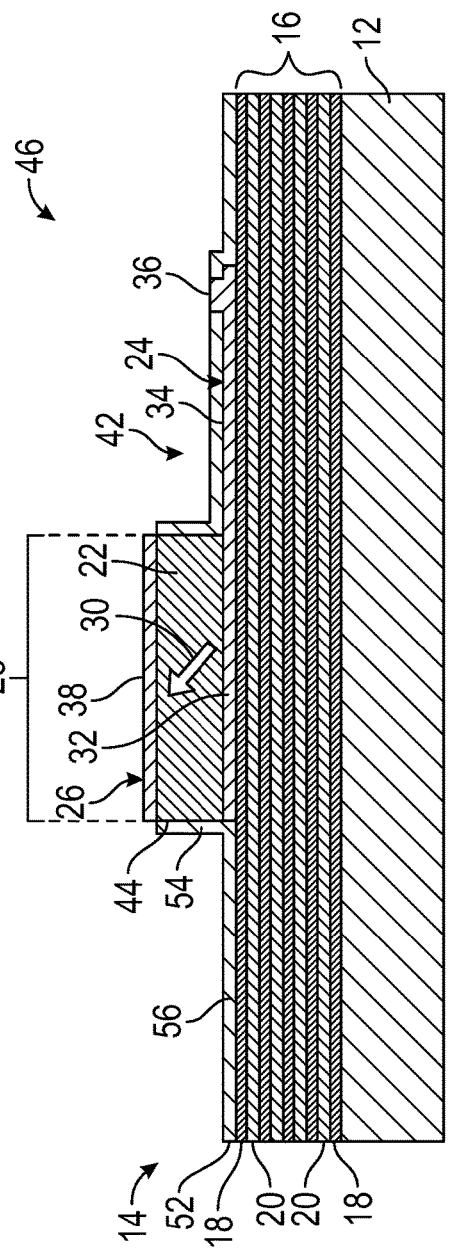
FIG. 2B
FIG. 2C

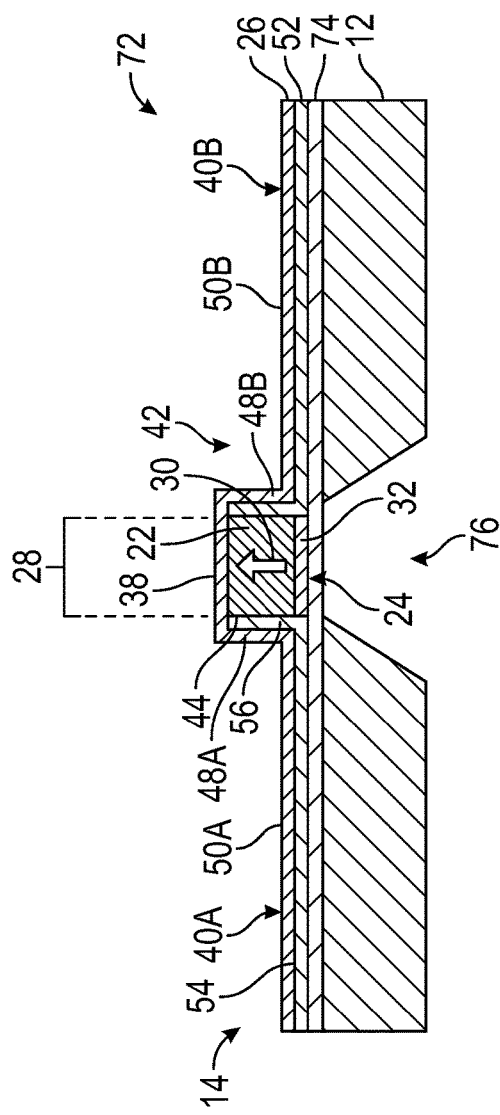
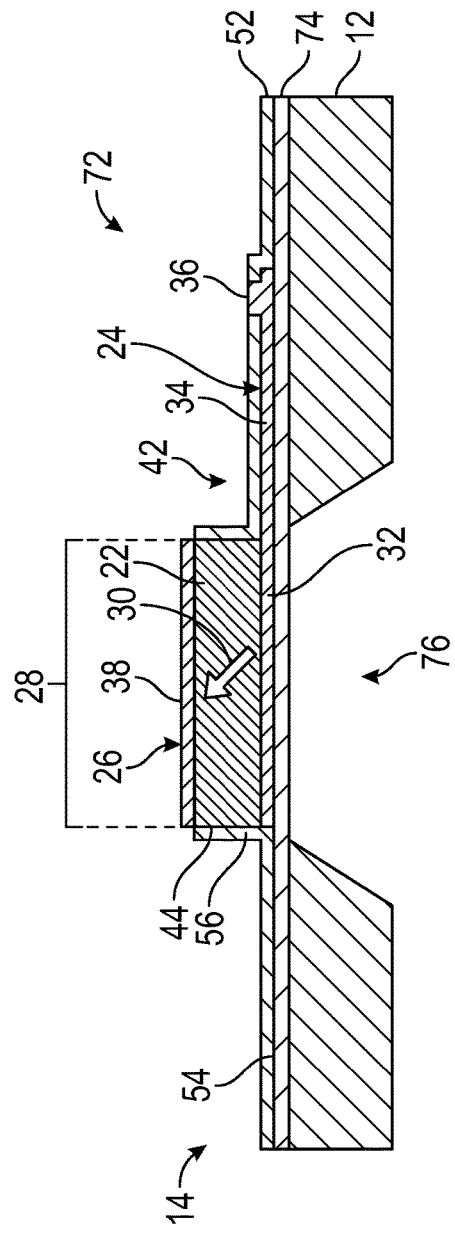
FIG. 6B
FIG. 6C

ACOUSTIC RESONATOR WITH REDUCED MECHANICAL CLAMPING OF AN ACTIVE REGION FOR ENHANCED SHEAR MODE RESPONSE

STATEMENT OF RELATED APPLICATIONS

This application claims the benefit of provisional patent application Ser. No. 62/257,954, filed Nov. 20, 2015, the disclosure of which is hereby incorporated herein by reference in its entirety.

TECHNICAL FIELD

The present disclosure relates to resonator structures, and in particular to bulk acoustic wave resonator structures with reduced mechanical confinement, such as may be usefully incorporated into fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods used with biosensors may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a functionalization (e.g., specific binding) material, whereby any changes to the characteristics of the propagation path affect the velocity and/or amplitude of the wave. Presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. Typically, BAW devices are fabricated by micro-electro-mechanical system (MEMS) fabrication techniques owing to the need to provide microscale features suitable for facilitating high frequency operation. BAW devices typically involve transduction of an acoustic wave using electrodes arranged on opposing top and bottom surfaces of a piezoelectric material. In a BAW device, three wave modes can propagate, namely: one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Fabricating a BAW resonator device may involve depositing an acoustic reflector over a substrate, followed by deposition of a bottom side electrode, followed by growth (e.g. via sputtering or other appropriate methods) of a piezoelectric material, followed by deposition of a top side electrode. Growth of the piezoelectric material could be by chemical vapor deposition (CVD), reactive RF magnetron sputtering (e.g., of Al ions in a nitrogen gas environment), etc. These techniques are capable of forming layers that are uniformly thick (e.g., piezoelectric material via sputtering), although some layers may have portions of differing heights depending on the topography of an underlying material deposition surface. For example, a bottom side electrode may not cover an entirety of the underlying acoustic reflector, such that a material deposition surface including the foregoing layers over a substrate may include bottom side electrode material that is slightly raised with respect to a top surface of the acoustic reflector. Upon application of a uniformly thick piezoelectric material over the material deposition surface, portions of the piezoelectric material positioned over the bottom side electrode will be raised relative to other portions of the piezoelectric material that are not overlying the bottom side electrode.

Modes of vibration in a solidly mounted resonator (SMR) type BAW devices are determined based on an assumption that the piezoelectric material is an infinite plate defined by dimensions of the electrodes arranged over and under the piezoelectric material forming an active region. Outside the active region, the BAW resonator device is mechanically clamped (e.g., mechanically restrained from freely moving) in the lateral direction due to presence of piezoelectric material bordering a periphery of the active region. For a BAW resonator device vibrating with mixed longitudinal and shear modes, this mechanical clamping has the potential to degrade a desired shear mode response in a plane of the piezoelectric material. In particular, such mechanical clamping tends to damp shear mode vibrations (e.g., shear mode response, shear displacement, etc.) of the active region, thereby limiting detection sensitivity and performance of the BAW resonator device.

Accordingly, there is a need for improved acoustic wave devices capable of enhanced shear mode vibrations, such as for biosensing or biochemical sensing applications, that overcome limitations associated with conventional devices.

SUMMARY

The present disclosure provides an acoustic resonator with reduced mechanical clamping of an active region for enhanced shear mode response. More specifically, the present disclosure provides a solidly mounted BAW resonator device with an active region of piezoelectric material laterally surrounded by an inactive region with a reduced thickness of piezoelectric material such that at least an upper portion of the inactive region along a boundary of the active region is devoid of piezoelectric material. The resonator device provides a discontinuity along opposing lateral edges of the piezoelectric material of the active region to reduce mechanical clamping of the active region in a direction of maximum lateral displacement in shear mode operation. Increasing the mechanical isolation of the active region of piezoelectric material of an acoustic wave resonator (e.g., a BAW) device decreases mechanical damping of lateral vibrations of the active region, which provides enhanced shear mode response that may beneficially enhance sensor performance in a liquid environment.

In one aspect, a micro-electrical-mechanical system (MEMS) resonator device includes: a substrate; and a bulk acoustic wave resonator structure arranged over at least a portion of the substrate, the bulk acoustic wave resonator structure including a piezoelectric material comprising a c-axis having an orientation distribution that is predominantly non-parallel to normal of a face of the substrate, a top side electrode arranged over the piezoelectric material, and a bottom side electrode arranged between the piezoelectric material and the substrate, wherein at least a portion of the piezoelectric material is arranged between the top side electrode and the bottom side electrode to form an active region; wherein the active region is laterally surrounded by an inactive region, and a thickness of piezoelectric material of at least a portion of the inactive region is less than a thickness of piezoelectric material of the active region, such that at least an upper portion of the inactive region along a boundary of the active region is devoid of piezoelectric material, defining at least one discontinuity along at least upper portions of opposing lateral edges of piezoelectric material of the active region, wherein the at least one discontinuity is configured to reduce mechanical clamping of the active region in a direction of maximum lateral displacement in shear mode operation of the bulk acoustic wave resonator structure.

In certain embodiments, the at least a portion of the piezoelectric material arranged between the top side electrode and the bottom side electrode comprises a nominal thickness; and at least a portion of a lateral perimeter of the active region is bounded by a reduced thickness portion of the piezoelectric material having a thickness in a range of from 0% to about 50% of the nominal thickness.

In certain embodiments, the active region comprises a length parallel to the direction of maximum lateral displacement in shear mode operation of the bulk acoustic wave resonator structure, the length extending between a first lengthwise end and a second lengthwise end of the active region; and the at least one discontinuity is bounded at least in part by the first lengthwise end and the second lengthwise end. In certain embodiments, the at least one discontinuity surrounds at least about 60% of a perimeter of the active region.

In certain embodiments, the bulk acoustic wave resonator structure comprises an acoustic reflector structure arranged between the substrate and the bottom side electrode. In certain embodiments, the substrate defines a cavity, and a support layer is arranged between the cavity and the bulk acoustic wave resonator structure.

In certain embodiments, the active region comprises a length parallel to the direction of maximum lateral displacement in shear mode operation of the bulk acoustic wave resonator structure; the active region comprises a width perpendicular to the length; and the length is greater than the width.

In certain embodiments, the active region comprises a length parallel to the direction of maximum lateral displacement in shear mode operation of the bulk acoustic wave resonator structure, and comprises a width perpendicular to the length; and the piezoelectric material comprises at least one anchor portion extending in a direction perpendicular to the length of the active region, and contacting the active region midway between lengthwise ends of the active region. In certain embodiments, at least a portion of at least one of the top side electrode or the bottom side electrode extends along the at least one anchor portion of the piezoelectric material. In certain embodiments, the MEMS resonator device further comprises a dielectric material arranged over lateral edges of the active region. In certain embodiments, a hermeticity layer is arranged over at least a portion of at least one of: the top side electrode, the bottom side electrode, or at least one lateral edge of the active region.

In certain embodiments, a fluidic device comprises the MEMS resonator device; at least one functionalization material arranged over at least a portion of the active region; and a fluidic channel containing the active region. In certain embodiments, the at least one functionalization material comprises at least one of a specific binding material or a non-specific binding material. In certain embodiments, the fluidic device further comprises a self-assembled monolayer arranged between the at least one functionalization material and the top side electrode. In certain embodiments, the fluidic device further comprises an interface layer arranged between the top side electrode and the self-assembled monolayer.

In another aspect, a method for biological or chemical sensing includes: supplying a fluid containing a target species into the fluidic channel of the fluidic device, wherein said supplying is configured to cause at least some of the target species to bind to the at least one functionalization material; inducing a bulk acoustic wave in the active region; and sensing a change in at least one of a frequency property, an amplitude-magnitude property, or a phase property of the bulk acoustic wave resonator structure to indicate at least one of presence or quantity of target species bound to the at least one functionalization material.

In another aspect, a method for fabricating a micro-electrical-mechanical system (MEMS) resonator device includes: forming a base structure including a substrate, a piezoelectric material arranged over at least a portion of the substrate and comprising a c-axis having an orientation distribution that is predominantly non-parallel to normal of a face of the substrate, and a bottom side electrode arranged between the substrate and at least a portion of the piezoelectric material, wherein the piezoelectric material comprises a nominal thickness; removing a portion of the piezoelectric material to define a reduced thickness portion of the piezoelectric material having a thickness in a range of from 0% to about 50% of the nominal thickness; and forming a top side electrode over a portion of the piezoelectric material, wherein at least a portion of the piezoelectric material comprising the nominal thickness is arranged between the top side electrode and the bottom side electrode to form an active region of a bulk acoustic wave resonator structure; wherein at least a portion of a lateral perimeter of the active region is bounded by the reduced thickness portion of the piezoelectric material, defining at least one discontinuity configured to reduce mechanical clamping of the active region in a direction of maximum lateral displacement in shear mode operation of the bulk acoustic wave resonator structure.

In certain embodiments, the method further comprises depositing a hermeticity layer over at least a portion of at least one of: the top side electrode, the bottom side electrode, or at least one lateral edge of the active region. In certain embodiments, the method further comprises forming a self-assembled monolayer over at least a portion of the top side electrode, and applying at least one functionalization material over at least a portion of the self-assembled monolayer, wherein at least a portion of the at least one functionalization material is registered with the active region.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 1B is a schematic cross-sectional view of the device of FIG. 1A taken along section line "A"-"A" of FIG. 1A.

FIG. 1C is a schematic cross-sectional view of the device of FIG. 1A taken along section line "B"-"B" of FIG. 1A.

FIG. 2B is a schematic cross-sectional view of the device of FIG. 2A taken along section line "C"-"C" of FIG. 2A.

FIG. 2C is a schematic cross-sectional view of the device of FIG. 2A taken along section line "D"-"D" of FIG. 2A.

FIG. 6B is a schematic cross-sectional view of the device of FIG. 6A taken along section line "I"-"I" of FIG. 6A.

FIG. 6C is a schematic cross-sectional view of the device of FIG. 6A taken along section line "J"-"J" of FIG. 6A.

DETAILED DESCRIPTION

Figure 1A:
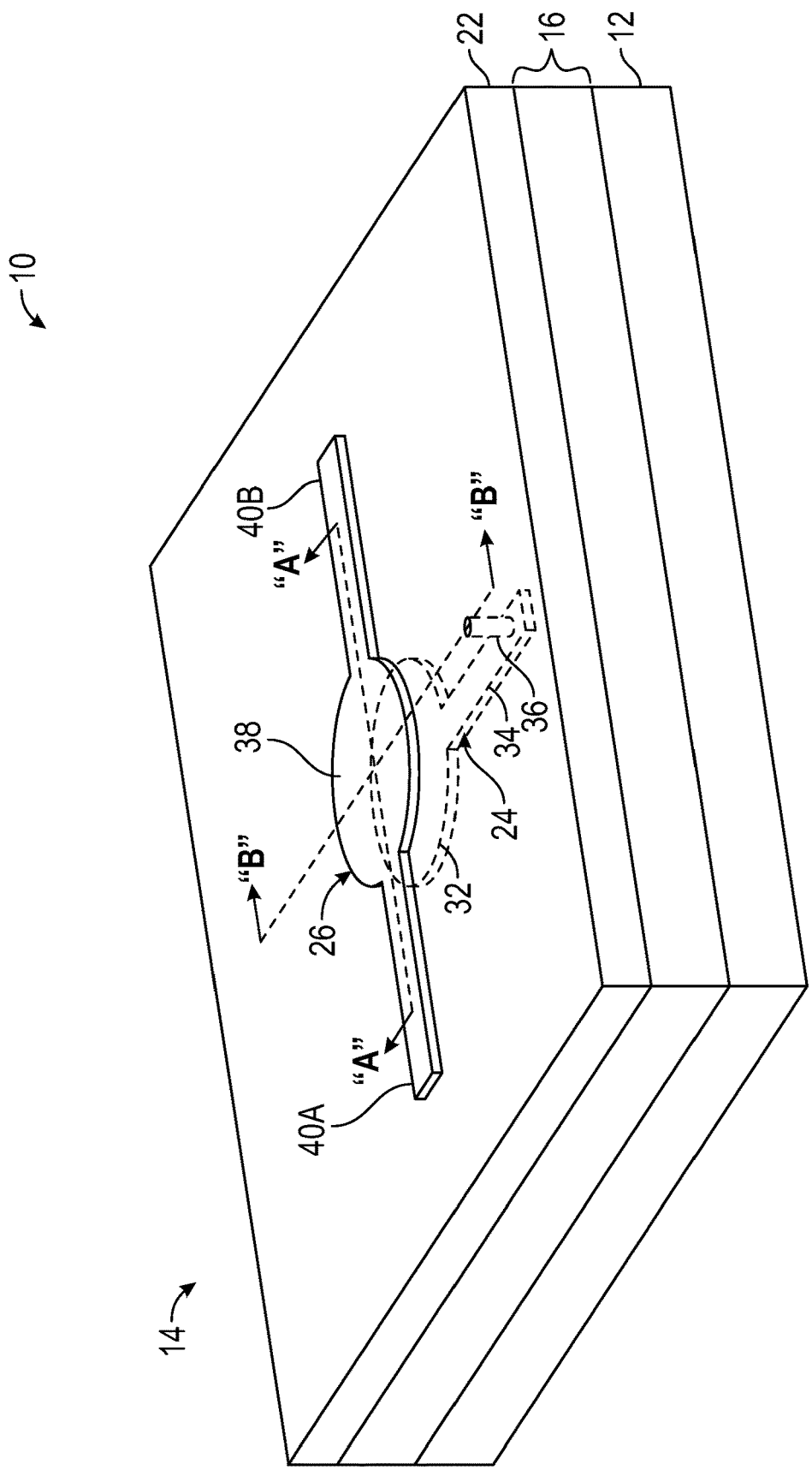
FIG. 1A is a schematic upper perspective view of at least a portion of a solidly mounted bulk acoustic wave (BAW) resonator device including piezoelectric material of an active region that is peripherally and continuously surrounded by a same thickness of piezoelectric material of an inactive region that contacts the active region, to serve as a comparison device intended to provide context for subsequently described embodiments of the present disclosure.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides an acoustic resonator with reduced mechanical clamping of an active region for enhanced shear mode response. More specifically, the present disclosure provides a solidly mounted BAW resonator device with an active region of piezoelectric material laterally surrounded by an inactive region with a reduced thickness of piezoelectric material, such that at least an upper portion of the inactive region along a boundary of the active region is devoid of piezoelectric material. The resonator device provides a discontinuity along opposing lateral edges of the piezoelectric material of the active region to reduce mechanical clamping of the active region in a direction of maximum lateral displacement in shear mode operation. Increasing the mechanical isolation of the active region of piezoelectric material of an acoustic wave resonator (e.g., a BAW) device decreases mechanical damping of lateral vibrations of the active region, which provides enhanced shear mode response that may beneficially enhance sensor performance in a liquid environment.

As discussed in more detail below, resonator devices according to embodiments disclosed herein include a substrate with a resonator structure mounted thereto. At least a bottom or lower portion of the resonator structure is clamped to the substrate, but at least an upper portion of an active region of the resonator structure is unconstrained along opposing lateral edge regions of piezoelectric material to reduce mechanical clamping. Restated, in certain embodiments, at least an upper portion of opposing lateral edge regions of piezoelectric material of the active region has a well-defined boundary with an air or liquid interface. The reduced mechanical clamping of the active region may serve to enhance shear mode vibration, thereby improving sensitivity and the limit of detection of the resonator device when sensing in a liquid environment. Electrical input and/or output connections to an active region of a resonator device with reduced mechanical clamping may be made using traces accessible at a top surface of the resonator device and/or using electrically conductive vias extending through a substrate (e.g., through silicon vias [TSVs] or the like).

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein. Before describing embodiments of the present disclosure providing reduced mechanical clamping of an active region, a comparison structure will be described (i.e., as illustrated in FIGS. 1A-1C).

FIGS. 1A-1C schematically illustrate at least a portion of a solidly mounted BAW resonator device 10 that serves as a comparison device intended to provide context for subsequently described embodiments of the present disclosure. The BAW resonator device 10 includes a substrate 12 (e.g., typically silicon or another semiconductor material) and a resonator structure 14 arranged over the substrate 12. The resonator structure 14 includes an acoustic reflector 16 (e.g., acoustic mirror) arranged over the substrate 12. The acoustic reflector 16 includes alternating low acoustic impedance layers 18 and high acoustic impedance layers 20, preferably bounded at top and bottom with low acoustic impedance layers 18, as shown in FIGS. 1B and 1C. In certain embodiments, an acoustic reflector 16 includes alternating layers 18, 20 of different materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used.

The resonator structure 14 further includes a piezoelectric material 22 arranged over the acoustic reflector 16, a bottom side electrode 24 arranged along a portion of a lower surface of the piezoelectric material 22 (i.e., between the acoustic reflector 16 and the piezoelectric material 22), and a top side electrode 26 arranged along a portion of an upper surface of the piezoelectric material 22. An area in which the piezoelectric material 22 is arranged between overlapping portions of the top side electrode 26 and the bottom side electrode 24 defines an active region 28 of the resonator device 10. The acoustic reflector 16 serves to reflect acoustic waves and therefore reduce or avoid dissipation of such waves in the substrate 12. Steps for forming the resonator device 10 may include depositing the acoustic reflector 16 over the substrate 12, followed by deposition of the bottom side electrode 24, followed by growth (e.g., via sputtering or other appropriate methods) of the piezoelectric material 22, followed by deposition of the top side electrode 26.

The piezoelectric material 22 may include aluminum nitride or zinc oxide material that includes a c-axis 30 (represented by a white arrow) having an orientation distribution that is predominantly non-parallel (and may also be non-perpendicular) to normal of a face of the substrate 12 (shown in FIG. 1C). Such a c-axis orientation distribution enables creation of shear displacements, which beneficially enables operation of the resonator device 10 with liquids, such as in a sensor and/or a microfluidic device. Although the c-axis 30 of the piezoelectric material 22 shown in FIG. 1B appears to be vertical in orientation, it is to be appreciated that the c-axis 30 is tilted away from the view, as is apparent upon review of FIG. 1C.

The bottom side electrode 24 comprises an active segment 32, a trace 34, and a conductive via 36 in conductive electrical communication with one another. The active segment 32 of the bottom side electrode 24 is generally circular, but could be any other shape (e.g., rectangular, elliptical, irregular polygonal, etc.). The trace 34 has a first end proximate to the active segment 32 and a second end proximate to the conductive via 36, and provides conductive electrical communication between the active segment 32 and the conductive via 36. The conductive via 36 extends upwardly through the piezoelectric material 22 (e.g., from a bottom surface to a top surface of the piezoelectric material 22).

The top side electrode 26 comprises an active central portion 38, a left trace 40A extending from a left side of the active central portion 38, and a right trace 40B extending from a right side of the active central portion 38. The active central portion 38 of the top side electrode 26 is generally circular but could be any other shape (e.g., rectangular, elliptical, irregular polygonal, etc.). The active segment 32 of the bottom side electrode 24 and the active central portion 38 of the top side electrode 26 may be approximately the same size and shape. The left trace 40A and right trace 40B extend in opposite directions. The top side electrode 26, particularly in the left trace 40A and right trace 40B, is configured to extend along a direction that is substantially perpendicular to an orientation of the bottom side electrode 24 (e.g., the trace 34 of the bottom side electrode 24).

As shown in FIGS. 1B and 1C, the active region 28 includes an active region boundary 44 and is surrounded on all sides by an inactive region 42. The piezoelectric material 22 continuously extends from the active region 28 to the inactive region 42. Due to this surrounding contact, the shear response (e.g., shear mode, shear vibrations, shear displacement, maximum lateral displacement in shear mode operation, etc.) of the piezoelectric material 22 in the active region 28 is damped by the piezoelectric material 22 in the inactive region 42, thereby limiting shear displacement and potentially limiting detection sensitivity and performance of the resonator device 10.

Having introduced the resonator device 10 as a comparison structure, embodiments of the present disclosure will now be described in connection with the remaining figures.

Figure 2A:
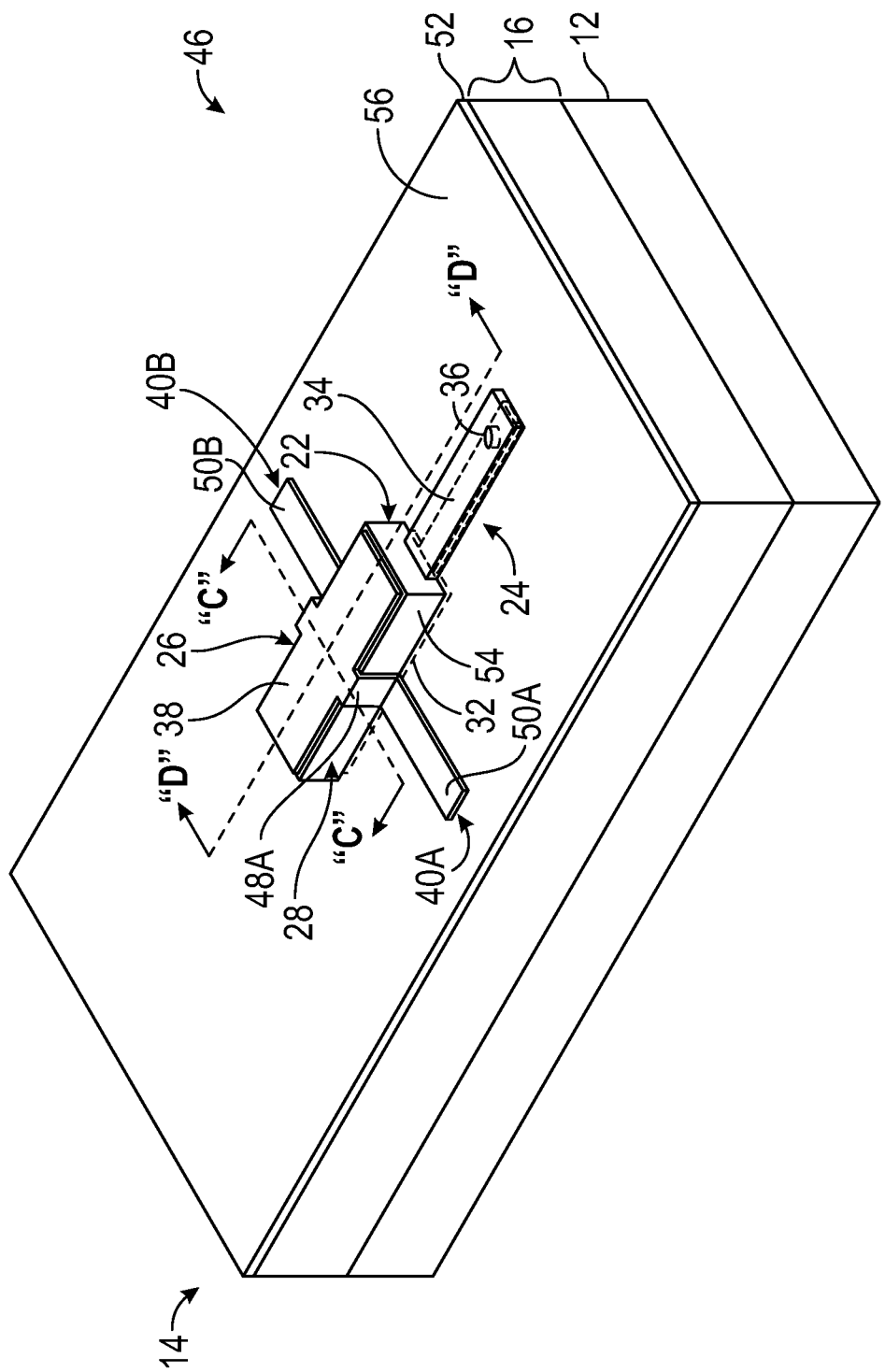
FIG. 2A is a schematic upper perspective view of at least a portion of a solidly mounted BAW resonator device according to one embodiment, with the BAW resonator device having a rectangular active region including a piezoelectric material and being laterally surrounded by an inactive region that is devoid of (i.e., includes zero thickness of) piezoelectric material, thereby providing a discontinuity along opposing lateral edges of the piezoelectric material of the active region to reduce mechanical clamping of the active region in a direction of maximum lateral displacement in shear mode operation.

FIGS. 2A-2C illustrate at least a portion of a solidly mounted BAW resonator device 46 according to one embodiment. The BAW resonator device 46 has a rectangular active region 28 that includes a piezoelectric material 22 and is laterally surrounded by an inactive region 42 devoid of (i.e., including zero thickness of) piezoelectric material. The piezoelectric material 22 resembles a mesa in appearance. Such configuration provides a discontinuity along opposing lateral edges of the piezoelectric material 22 of the active region 28 to reduce mechanical clamping of the active region 28 in a direction of maximum lateral displacement in shear mode operation (e.g., in a direction from left to right of the active region 28 shown in FIG. 2C).

The BAW resonator device 46 includes a substrate 12 (e.g., typically silicon or another semiconductor material) and a resonator structure 14 arranged over the substrate 12. The resonator structure 14 includes an acoustic reflector 16 arranged over the substrate 12. The acoustic reflector 16 includes alternating low acoustic impedance layers 18 and high acoustic impedance layers 20, as shown in FIGS. 2B and 2C. In certain embodiments, an acoustic reflector 16 includes alternating thin layers 18, 20 of different materials (e.g., SiOC, Si$_3$N$_4$, SiO$_2$, AlN, W, and Mo), optionally embodied in a quarter-wave Bragg mirror, deposited over the substrate 12. In certain embodiments, other types of acoustic reflectors may be used.

The resonator structure 14 further includes the piezoelectric material 22 arranged over the acoustic reflector 16, a bottom side electrode 24 arranged along a portion of a lower surface of the piezoelectric material 22 (between the acoustic reflector 16 and the piezoelectric material 22), and a top side electrode 26 arranged along a portion of an upper surface of the piezoelectric material 22. An area in which the piezoelectric material 22 is arranged between overlapping portions of the top side electrode 26 and the bottom side electrode 24 defines the active region 28 of the BAW resonator device 46. The acoustic reflector 16 serves to reflect acoustic waves and therefore reduce or avoid dissipation of such waves in the substrate 12. The piezoelectric material 22 arranged between the top side electrode 26 and the bottom side electrode 24 has a nominal thickness. Steps for forming the BAW resonator device 46 may include depositing the acoustic reflector 16 over the substrate 12, followed by deposition of the bottom side electrode 24, followed by growth (e.g., via sputtering or other appropriate methods) of the piezoelectric material 22, followed by deposition of the top side electrode 26.

In certain embodiments, the piezoelectric material 22 comprises aluminum nitride or zinc oxide material that includes a c-axis 30 having an orientation distribution that is predominantly non-parallel (and may also be non-perpendicular) to normal of a face of the substrate 12 (e.g., shown in FIG. 2C). Such a c-axis orientation distribution enables creation of shear displacements, which beneficially enable operation of the BAW resonator device 46 with liquids, such as in a sensor and/or a microfluidic device. The bottom side electrode 24 comprises an active segment 32, a trace 34, and an electrically conductive via 36. The active segment 32 of the bottom side electrode 24 is generally circular but could be any other shape (e.g., rectangular, elliptical, irregular polygonal, etc.). The trace 34 has a first end proximate to the active segment 32 and a second end opposite to the first end proximate to the via 36. Thus, the trace 34 provides conductive electrical communication between the active segment 32 and the via 36 (vertically extending through one or more layers to a top surface). The bottom side electrode 24, particularly the trace 34, is configured to extend along a first direction (e.g., from front to back in FIG. 2B, or from left to right in FIG. 2C) in the same direction as a direction of maximum displacement of the active region 28 in shear mode operation.

The top side electrode 26 includes an active central portion 38, a left trace 40A extending from a left side of the active central portion 38, and a right trace 40B extending from a right side of the active central portion 38. The active central portion 38 of the top side electrode 26 is generally circular but could be any other shape (e.g., rectangular, elliptical, irregular polygonal, etc.). The active segment 32 of the bottom side electrode 24 and the active central portion 38 of the top side electrode 26 may be approximately the same size and shape. The left trace 40A and right trace 40B extend in opposite directions. The top side electrode 26, particularly in left trace 40A and right trace 40B, is configured to extend along a second direction (e.g., from left to right) perpendicular to the first direction. In this way, the top side electrode 26 extends in a direction perpendicular to that of the c-axis 30 and/or bottom side electrode 24 (e.g., the trace 34 of the bottom side electrode 24).

The bottom side electrode 24 and top side electrode 26 could be a single metal or a bi-layer metal. A bi-layer structure could be used to improve electrical performance or act as an etch stop layer, thereby protecting the bottom side electrode 24 when defining laterally etched features.

As shown in FIGS. 2A-2C, the active region 28 (e.g., including the piezoelectric material 22, the active segment 32 of the bottom side electrode 24, and the active central portion 38 of the top side electrode 26) includes an active region boundary 44 and is rectangular in shape, although an active region may be provided in any other desired shape (e.g., circle, ellipse, etc.). The shape of the active region 28 can be optimized based on shear mode wave propagation direction and maximum surface displacement at the frequency of interest. When an active region embodies a rectangular or elliptical shape, the length-to-width ratio can be optimized to enhance shear wave propagation of the BAW resonator device 46. A desired wavelength of an acoustic wave to be induced may also be considered in optimizing the dimensions of an active region of a resonator device. With continued reference to FIGS. 2A-2C, the rectangular active region 28 is oriented such that the length of the active region 28 (the length being wider than the width) is oriented in one direction (e.g., the shear direction, extending from front to back in FIG. 2B, and extending from left to right in FIG. 2C), and a width of the active region 28 is oriented in another direction that is perpendicular to the one direction.

In the embodiment shown in FIGS. 2A-2C, the piezoelectric material 22 embodies a mesa and its presence is limited to the active region 28. Restated, the piezoelectric material 22 laterally extends only to the active region boundary 44. The inactive region 42 of the BAW resonator device 46 surrounds the active region 28. The thickness of the piezoelectric material 22 in the inactive region 42 is zero (therefore less than the thickness of the piezoelectric material 22 in the active region 28), such that an entirety of the inactive region 42 (including an upper portion thereof) is devoid of piezoelectric material 22 In other words, the piezoelectric material 22 present in the active region 28 has a nominal thickness, and at least a portion of the piezoelectric material 22 in the inactive region 42 (e.g., beyond opposing sides of the active region 28) may have a thickness in a range of from 0% to about 50% of the nominal thickness. This thickness difference defines a discontinuity of piezoelectric material 22 along an upper portion of the sides (e.g., opposing lateral edges) of the piezoelectric material 22 of the active region 28. In certain embodiments, a discontinuity of piezoelectric material 22 is provided around at least about 60% of a perimeter of the active region 28. The lack of piezoelectric material in the inactive region 42 in contact with at least an upper portion of the piezoelectric material 22 of the active region 28 results in the active region 28 experiencing reduced mechanical clamping in a direction (e.g., the first direction) of maximum lateral displacement in shear mode operation of the BAW resonator device 46. In alternative embodiments, piezoelectric material 22 may be reduced in the inactive region 42 to a non-zero amount, and may continuously extend from the piezoelectric material 22 in the active region 28 to provide reduced mechanical clamping of the active region 28.

With continued reference to FIGS. 2A-2C, the left trace 40A of the top side electrode 26 includes a vertical portion 48A and a horizontal portion 50A, and the right trace 40B of the top side electrode 26 includes a vertical portion 48B and a horizontal portion 50B. To prevent electrical contact between the top side electrode 26 and the bottom side electrode 24, the BAW resonator device 46 includes an electrically insulating barrier layer 52 (e.g., aluminum oxide [$Al_2O_3$] deposited by ALD) comprising a vertical portion 54 and a horizontal portion 56. The barrier layer 52 is arranged generally below portions of the top side electrode 26, except under the active central portion 38 coinciding with the active region 28. The vertical portion 54 of the barrier layer 52 extends around at least a portion of the lateral surface of the active region 28, and extends upward to at least a height of the lateral surface of the active region 28. The horizontal portion 56 of the barrier layer 52 is positioned to cover at least a portion of the acoustic reflector 16. In certain embodiments, it is anticipated that the barrier layer 52 could be configured to be thicker than the bottom side electrode 24, such that a vertical portion 54 may be omitted from the barrier layer 52, but the top side electrode 26 would still be prevented from contacting the bottom side electrode 24. As noted previously, the barrier layer 52 is not present between the active central portion 38 of the top side electrode 26 and the piezoelectric material layer 22 (e.g., by initially depositing the barrier layer 52 over an entire deposition surface, followed by selectively etching the barrier layer 52 away from the active region 28), so as to avoid degradation of the resonator quality factor (Q). It is noted that the piezoelectric material 22 in the active region 28 may have angled lateral walls (e.g., wider at the base than the top), and in such an instance, the left and right vertical portions 48A, 48B of the top side electrode 26, and/or the vertical portion 54 of the barrier layer 52, would also be angled to follow lateral contours of the piezoelectric material 22 in the active region 28.

Figure 3A:
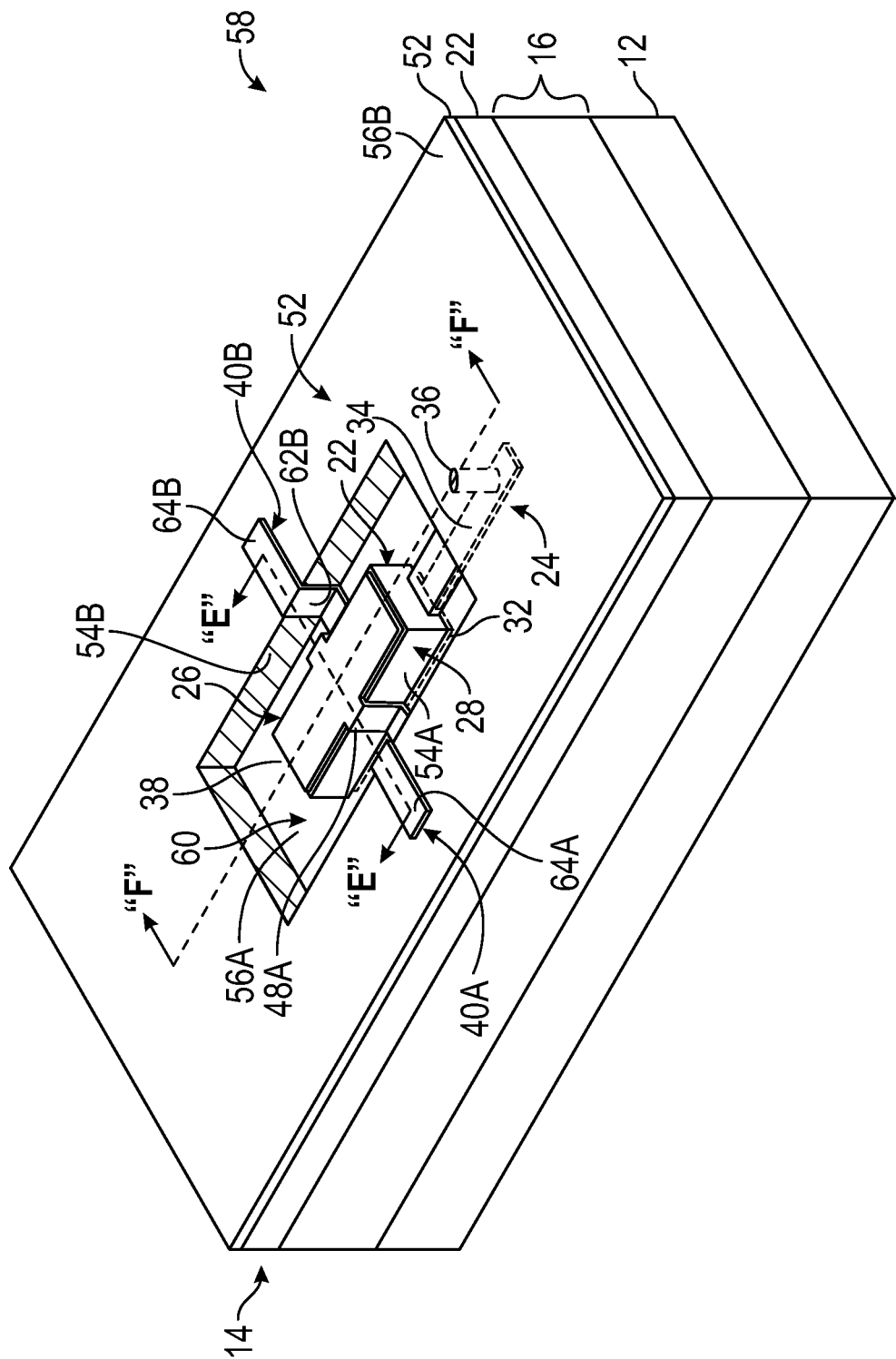
FIG. 3A is a schematic upper perspective view of at least a portion of a solidly mounted BAW resonator device according to another embodiment, with the BAW resonator device having a rectangular active region including a piezoelectric material and being laterally surrounded by an inactive region that is devoid of (i.e., includes zero thickness of) piezoelectric material in a single recess surrounding the active region, with traces for a top side electrode extending along side walls and a floor of the single recess, and with the single recess providing a discontinuity along opposing lateral edges of the active region to reduce mechanical clamping of the active region in a direction of maximum displacement in shear mode operation.
Figure 3B:
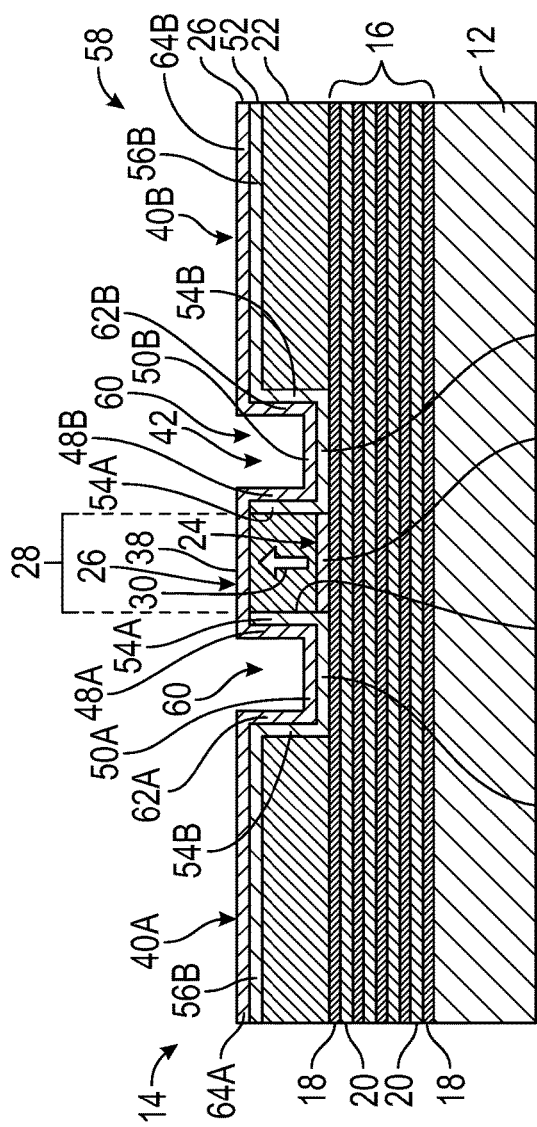
FIG. 3B is a schematic cross-sectional view of the device of FIG. 3A taken along section line "E"-"E" of FIG. 3A.
Figure 3C:
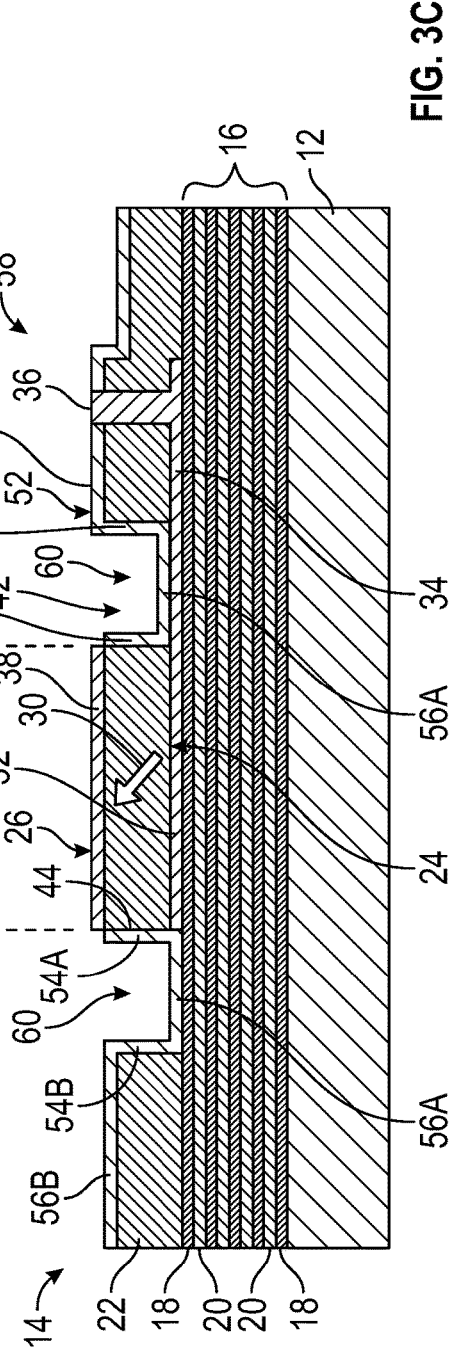
FIG. 3C is a schematic cross-sectional view of the device of FIG. 3A taken along section line "F"-"F" of FIG. 3A.

FIGS. 3A-3C illustrate at least a portion of a solidly mounted BAW resonator device 58 according to another embodiment, with a rectangular active region 28 resembling a recessed or sunken mesa and being surrounded by a continuous single recess 60. The rectangular active region 28 includes a piezoelectric material 22 and is laterally surrounded by an inactive region 42 devoid of (i.e., including zero thickness of) piezoelectric material 22 within the single recess 60 surrounding the active region 28. Left and right electrical traces 40A, 40B in conductive electrical communication with a top side electrode 26 extend along side walls and the floor of the single recess 60. The single recess 60 provides a discontinuity along opposing lateral edges of the active region 28 to reduce mechanical clamping of the active region 28 in a direction of maximum displacement in shear mode operation (e.g., parallel to a lengthwise direction of the active region 28). FIG. 3A includes cross-hatching for illustrative purposes only.

As with the embodiment of FIGS. 2A-2C, the BAW resonator device 58 shown in FIGS. 3A-3C includes a substrate 12 and a resonator structure 14 arranged over the substrate 12, with an acoustic reflector 16 arranged therebetween. The acoustic reflector 16 includes alternating low acoustic impedance layers 18 and high acoustic impedance layers 20 (shown in FIGS. 3B and 3C). The resonator structure 14 further includes a bottom side electrode 24 arranged over a portion of the acoustic reflector 16, the piezoelectric material 22 arranged over the bottom side electrode 24 as well as the acoustic reflector 16, and the top side electrode 26 arranged over portions of the piezoelectric material 22. The piezoelectric material 22 includes a c-axis 30 having an orientation distribution that is predominantly non-parallel to normal of a face of the substrate 12. The bottom side electrode 24 comprises an active segment 32, a trace 34, and an electrically conductive via 36, and the top side electrode includes an active central portion 38. The resonator structure 14 also includes the active region 28 defined by a portion of the piezoelectric material 22 arranged between the bottom side electrode 24 and the top side electrode 26, with the inactive region 42 generally surrounding the active region 28. An active region boundary 44 represents a lateral extent of the active region 28. An electrically insulating barrier layer 52 is further provided over portions of the BAW resonator device 58.

The single recess 60 is defined between piezoelectric material 22 in the active region 28 and piezoelectric material 22 in the inactive region 42. In other words, the piezoelectric material 22 of the active region 28 laterally extends to the active region boundary 44, where it discontinues (e.g., is absent), and the piezoelectric material 22 continues again in the inactive region 42. As shown in FIG. 3A, the piezoelectric material 22 of the inactive region 42 is provided in a shape resembling a rectangular frame surrounding the single recess 60, which surrounds the active region 28. The thickness of the piezoelectric material 22 in the single recess 60 of the inactive region 42 reduces to zero (thereby embodying a value less than the thickness of the piezoelectric material 22 in the active region 28), such that an entirety of the single recess 60 (including an upper portion of the inactive region 42 bounding the active region 28) is devoid of piezoelectric material 22. In other words, the piezoelectric material 22 in the active region 28 has a nominal thickness, and at least a portion of the piezoelectric material 22 in the inactive region 42 (i.e., in the single recess 60, including opposing sides of the active region 28) has zero percent of the nominal thickness of piezoelectric material 22. This defines a discontinuity of piezoelectric material 22 along an upper portion of sides (e.g., opposing lateral edges) of the piezoelectric material 22 of the active region 28 (e.g., extending along a majority of a perimeter of the active region 28, such as at least about 60%, at least about 80%, or at least about 100% of the perimeter of the active region 28). Accordingly, the active region 28 experiences reduced mechanical clamping in a direction (e.g., the first direction) of maximum lateral displacement in shear mode operation of the BAW resonator device 58. In certain embodiments, piezoelectric material 22 is reduced in the inactive region 42 bounding the active region 28 to a non-zero amount (e.g., to a thickness of up to 50% of the nominal thickness), and continuously extends from the piezoelectric material 22 in the active region 28, to provide reduced mechanical clamping of the active region 28.

With continued reference to FIGS. 3A-3C, the left trace 40A of the top side electrode 26 includes an inner vertical portion 48A, an outer vertical portion 62A, a lower horizontal portion 50A, and an upper horizontal portion 64A. The right trace 40B of the top side electrode 26 similarly includes an inner vertical portion 48B, an outer vertical portion 62B, a lower horizontal portion 50B, and an upper horizontal portion 64B.

To prevent electrical contact between the top side electrode 26 and the bottom side electrode 24, the barrier layer 52 (e.g., aluminum oxide [$Al_2O_3$]) is provided. The barrier layer 52 includes an inner vertical portion 54A, an outer vertical portion 54B, a lower horizontal portion 56A, and an upper horizontal portion 56B. The lower horizontal portion 56A of the barrier layer 52 is arranged between the acoustic reflector 16 and the lower horizontal portions 50A, 50B of the left and right traces 40A, 40B of the top side electrode 26. The inner vertical portion 54A of the barrier layer 52 is arranged between (i) lateral sides of each of the piezoelectric material 22 and the bottom side electrode 24 and (ii) left and right inner vertical portions 48A, 48B of the top side electrode 26. The outer vertical portion 54B of the barrier layer 52 is arranged between (i) the outer vertical portions 62A, 62B of the left and right traces 40A, 40B of the top side electrode 26 and (ii) the piezoelectric material 22 in the inactive region 42.

The inner vertical portion 54A of the barrier layer 52 extends around at least a portion of the lateral surface of the active region 28, and extends upward to at least a height of the lateral surface of the active region 28. In certain embodiments, it is anticipated that the barrier layer 52 could be configured to be thicker than the bottom side electrode 24, such that the inner vertical portion 54A, outer vertical portion 54B, and/or upper horizontal portion 56B could be omitted, but electrical contact would still be prevented between the top side electrode 26 and the bottom side electrode 24.

Although FIGS. 3A-3C illustrate the single recess 60 laterally surrounding the active region 28, it is to be appreciated that in certain embodiments, multiple recesses (or recess portions) including a reduced thickness of piezoelectric material (e.g., reduced by 50% to 100% relative to a nominal thickness of piezoelectric material in an active region) may be arranged along a periphery of an active region to reduce mechanical clamping. For example, first and second substantially C-shaped or substantially U-shaped recesses may be arranged along a periphery of the active region. Recesses according to other configurations may be provided. Preferably, at least a majority of a perimeter of an active region (such as at least about 60%, at least about 80%, or at least about 100% of the perimeter of an active region) is bounded by an inactive region having a reduced thickness of piezoelectric material.

Figure 4A:
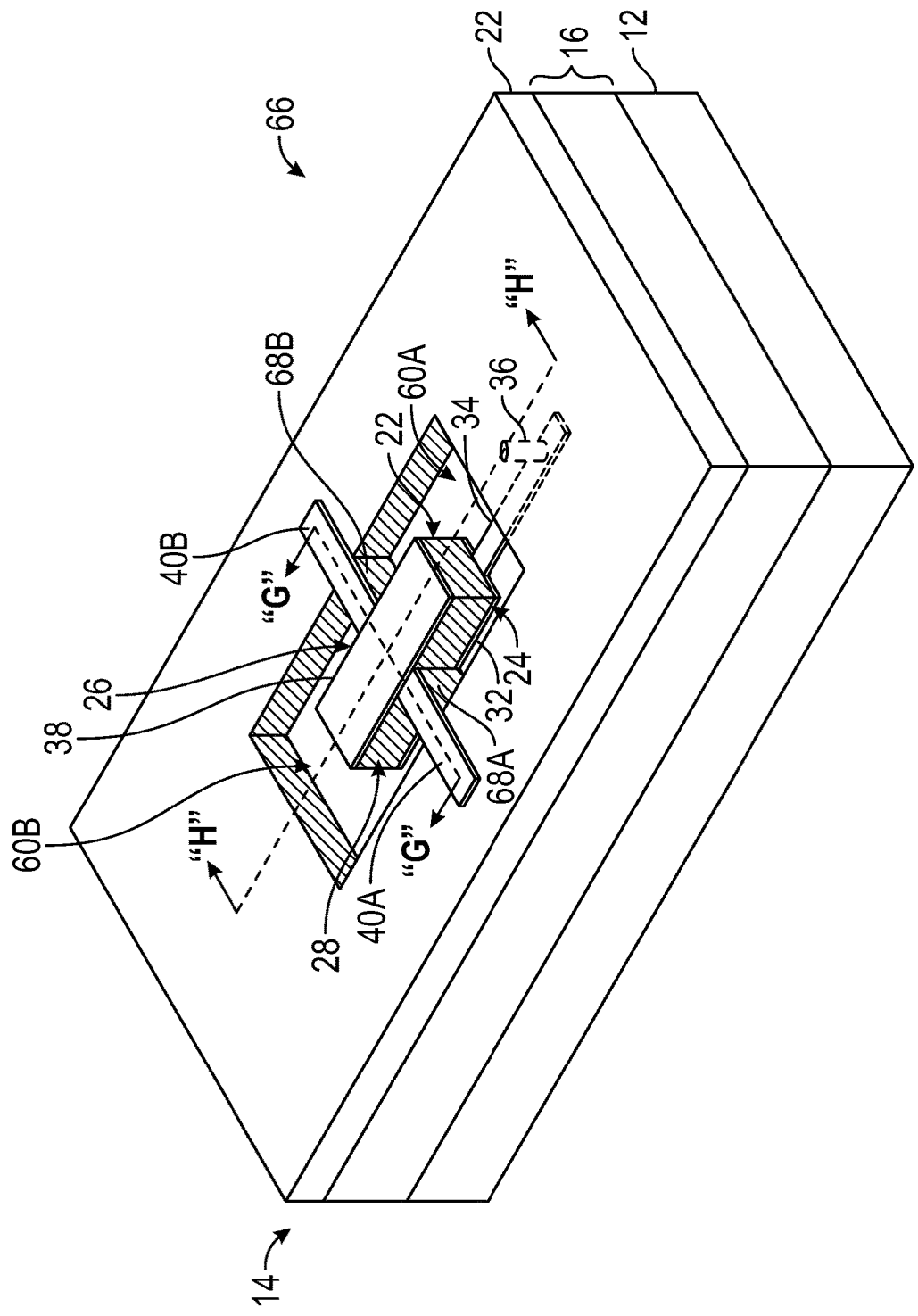
FIG. 4A is a schematic upper perspective view of at least a portion of a solidly mounted BAW resonator device according to another embodiment, with the BAW resonator device having a rectangular active region including a piezoelectric material that is devoid of (i.e., includes zero thickness of) piezoelectric material in first and second recess portions separated by piezoelectric material anchors, with traces for a top side electrode extending along top surfaces of the anchors, and with the first and second recess portions providing a discontinuity along opposing lateral edges of the active region in a direction of maximum displacement in shear mode operation.
Figure 4B:
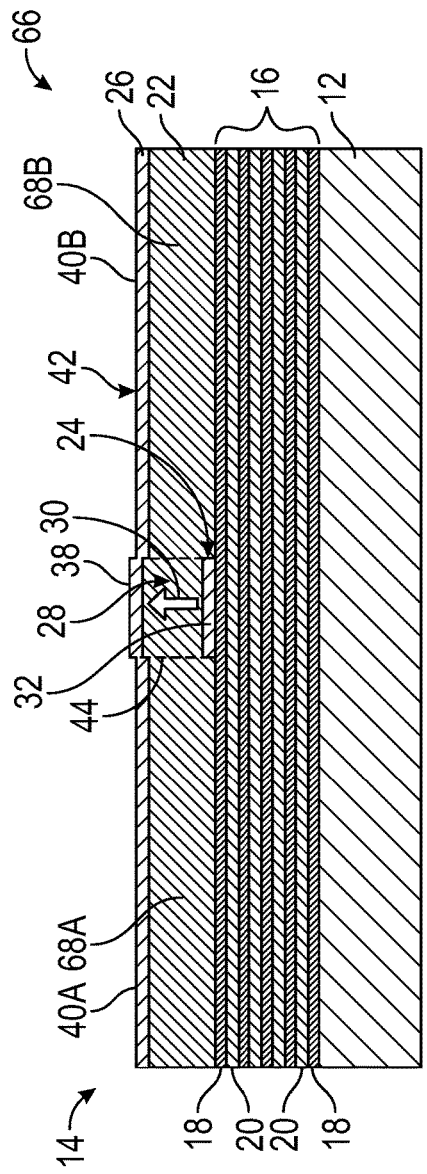
FIG. 4B is a schematic cross-sectional view of the device of FIG. 4A taken along section line "G"-"G" of FIG. 4A.
Figure 4C:
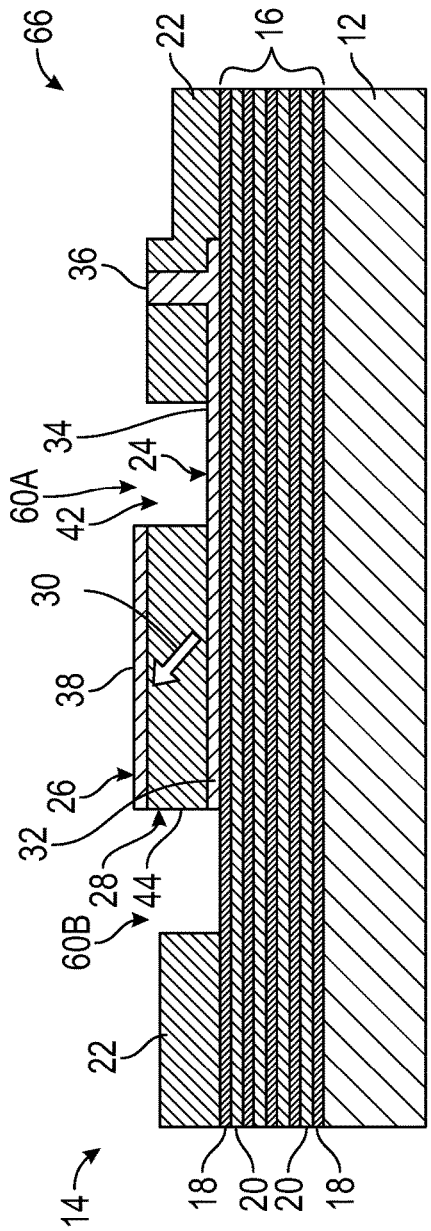
FIG. 4C is a schematic cross-sectional view of the device of FIG. 4A taken along section line "H"-"H" of FIG. 4A.

FIGS. 4A-4C illustrate at least a portion of a solidly mounted BAW resonator device 66 according to another embodiment, with a majority of a rectangular active region 28 being peripherally surrounded by two discontinuous first and second recesses (or recess portions) 60A, 60B separated by piezoelectric material left and right anchors 68A, 68B. The recesses 60A, 60B are devoid of (i.e., include zero thickness of) a piezoelectric material 22, and provide a discontinuity along opposing lateral edges of the active region 28 in a direction of maximum displacement in shear mode operation. Traces 40A, 40B for a top side electrode 26 extend along top surfaces of the anchors 68A, 68B, and with the first and second recesses 60A, 60B providing a discontinuity along opposing lateral edges of the active region 28 in a direction of maximum displacement in shear mode operation (e.g., a first direction extending in a front to back direction in FIG. 4B, or in a side-to-side direction in FIG. 4C). The piezoelectric material 22 includes a c-axis 30 having an orientation distribution that is predominantly non-parallel to normal of a face of the substrate 12. The bottom side electrode 24 comprises an active segment 32, a trace 34, and an electrically conductive via 36, while the top side electrode includes an active central portion 38. FIG. 4A includes cross-hatching for illustrative purposes only.

As with the embodiments of FIGS. 2A-2C and FIGS. 3A-3C, the BAW resonator device 66 shown in FIGS. 4A-4C includes a substrate 12 and a resonator structure 14 arranged over the substrate 12, with an acoustic reflector 16 arranged therebetween. The acoustic reflector 16 includes alternating low acoustic impedance layers 18 and high acoustic impedance layers 20 (shown in FIGS. 4B and 4C). The resonator structure 14 further includes a bottom side electrode 24 arranged over a portion of the acoustic reflector 16, a piezoelectric material 22 arranged over the bottom side electrode 24 as well as the acoustic reflector 16, and a top side electrode 26 arranged over portions of the piezoelectric material 22. The resonator structure 14 also includes the active region 28 defined by a portion of the piezoelectric material 22 arranged between the bottom side electrode 24 and the top side electrode 26, with an inactive region 42 generally surrounding the active region 28. An active region boundary 44 represents a lateral extent of the active region 28.

First and second recesses 60A, 60B are defined between piezoelectric material 22 in the active region 28 and piezoelectric material 22 in the inactive region 42, with the recesses 60A, 60B being separated by the anchors 68A, 68B. In other words, the piezoelectric material 22 laterally extends to the active region boundary 44, where it discontinues (e.g., is absent), and the piezoelectric material 22 continues again in the inactive region 42 (except at anchors 68A, 68B discussed in more detail below). Excluding the anchors 68A, 68B, the thickness of the piezoelectric material 22 in the recesses 60A, 60B of the inactive region 42 reduces to zero (thereby embodying a value less than the thickness of the piezoelectric material 22 in the active region 28), such that an entirety of each recess 60A, 60B (including an upper portion of the inactive region 42 bounding the active region 28) is devoid of piezoelectric material 22. In other words, the piezoelectric material 22 in the active region 28 has a nominal thickness, and at least a portion of the piezoelectric material 22 in the inactive region 42 (i.e., in the recesses 60A, 60B, including opposing sides of the active region 28) has zero percent of the nominal thickness. This defines a discontinuity of piezoelectric material 22 along an upper portion of sides (e.g., opposing lateral edges) of the piezoelectric material 22 of the active region 28, (e.g., extending a majority of a perimeter of the active region 28, such as at least about 60%, at least about 80%, or at least about 90% of the perimeter of the active region 28). Accordingly, the active region 28 experiences reduced mechanical clamping in a direction (e.g., the first direction) of maximum lateral displacement in shear mode operation of the BAW resonator device 46. In certain embodiments, piezoelectric material 22 is reduced in the inactive region 42 bounding the active region 28 to a non-zero amount (e.g., to a thickness of up to 50% of the nominal thickness), and continuously extends from the piezoelectric material 22 in the active region 28, to provide reduced mechanical clamping of the active region 28.

Unlike the preceding two embodiments, the BAW resonator device 66 shown in FIGS. 4A-4C does not require a barrier layer to provide electrical insulation between top side and bottom side electrodes 26, 24. Instead, the BAW resonator device 66 includes left and right anchors 68A, 68B over which portions of the left and right traces 40A, 40B of the top side electrode 26 extend to provide conductive electrical communication with an active central portion 38 of the top side electrode 26. The top side electrode 26 cannot accidentally contact the bottom side electrode 24 because the left and right anchors 68A, 68B are positioned therebetween. Each of the left anchor 68A and the right anchor 68B includes piezoelectric material that continuously extends from a side of the active region 28 to the piezoelectric material 22 in the inactive region 42 that substantially surrounds the active region 28. The left and right anchors 68A, 68B also represent boundaries between the first and second recesses 60A, 60B.

The left anchor 68A and right anchor 68B are arranged on opposite sides of the active region 28 (approximately midway between lengthwise ends thereof), and extend in a second direction perpendicular to the first direction. When the active region 28 experiences dominant shear mode vibration, lengthwise ends of the active region 28 undergo displacement in the first direction (e.g., a first direction extending in a front to back direction in FIG. 4B, or in a side-to-side direction in FIG. 4C), but a medial plane positioned at a center of the active region 28 (e.g., extending through the left and right anchors 68A, 68B at a midpoint between the lengthwise ends of the active region 28) may be static. Thus, attachment of the anchors 68A, 68B to piezoelectric material 22 forming lateral sides of the active region 28 at a midpoint between the lengthwise ends of the active region 28 does not significantly impede lateral displacement of the active region 28 when undergoing shear mode vibration. Dimensions of the anchors 68A, 68B can be optimized to enable sufficient electrical current to pass through top side portions of the left and right traces 40A, 40B of the top side electrode 26 while minimizing mechanical impedance of shear mode vibration. In particular, the smaller the anchors 68A, 68B (e.g., width, height, etc.), the less mechanical clamping will be experienced by the active region 28, but mechanical support and electrical current handling limitations should also be considered. By orienting a c-axis 30 of the piezoelectric material 22 with a direction of maximum displacement in shear mode operation perpendicular to the left and right anchors 68A, 68B, mechanical damping is minimized and shear mode response may be improved.

Figure 5:
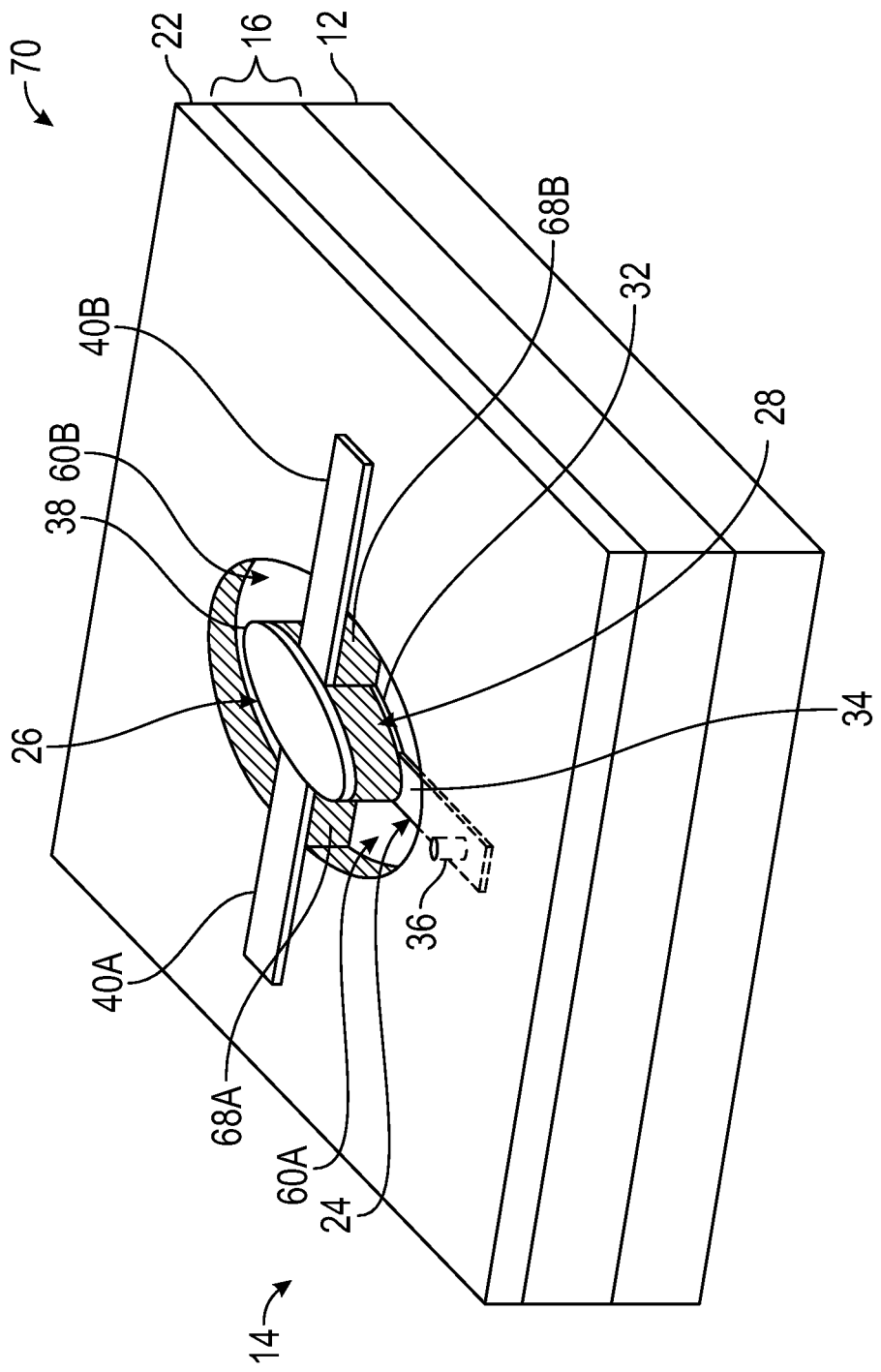
FIG. 5 is a schematic upper perspective view of at least a portion of a solidly mounted BAW resonator device according to another embodiment, with the BAW resonator device having an elliptical active region including a piezoelectric material that is devoid of (i.e., includes zero thickness of) piezoelectric material in first and second recess portions separated by piezoelectric material anchors, with traces for a top side electrode extending along top surfaces of the anchors, and with the first and second recess portions providing a discontinuity along opposing lateral edges of the active region in a direction of maximum displacement in shear mode operation.

In certain embodiments, BAW resonator devices may include active regions that are non-rectangular in shape. FIG. 5 is a schematic upper perspective view of at least a portion of a solidly mounted BAW resonator device 70 that is similar to the BAW resonator device 66 shown in FIGS. 4A-4C, but has an elliptical active region 28. The BAW resonator device 70 includes a substrate 12 and a resonator structure 14 arranged over the substrate 12, with an acoustic reflector 16 arranged therebetween. The resonator structure 14 further includes a bottom side electrode 24 arranged over a portion of the acoustic reflector 16, a piezoelectric material 22 arranged over the bottom side electrode 24 as well as the acoustic reflector 16, and a top side electrode 26 arranged over portions of the piezoelectric material 22. The piezoelectric material 22 includes a c-axis 30 having an orientation distribution that is predominantly non-parallel to normal of a face of the substrate 12. The bottom side electrode 24 comprises an active segment 32, a trace 34, and an electrically conductive via 36, and the top side electrode includes an active central portion 38 that is surrounded by discontinuous first and second recesses (or recess portions) 60A, 60B that separated by piezoelectric material anchors 68A, 68B. The recesses 60A, 60B are devoid of (i.e., include zero thickness of) piezoelectric material 22. Electrical traces 40A, 40B for the top side electrode 26 extend along top surfaces of the anchors 68A, 68B, with first and second recesses 60A, 60B providing a discontinuity along opposing lateral edges of the active region 28 in a direction of maximum displacement in shear mode operation. FIG. 5 includes cross-hatching for illustrative purposes only.

It is to be recognized that an active region of a BAW resonator device disclosed herein (e.g., including any of the previously disclosed embodiments) may be provided in any suitable shape (e.g., circular, rectangular, oval, trapezoidal, irregular polygonal, etc.). In certain embodiments, an active region may be shaped as an irregular polygon (e.g., irregular quadrilateral) with no equal or parallel sides. Avoiding lateral symmetry in the shape of an active region may beneficially reduce the presence of lateral standing waves. The above-mentioned symmetry corresponds to the footprint of the active region, and avoiding lateral symmetry corresponds to avoiding symmetry associated with the sides of the footprint. For example, a footprint that corresponds to a pentagon instead of a square or rectangle may be selected. The avoidance of lateral symmetry, also known as apodization, may be used to suppress spurious modes that fall below the series resonance frequency ($f_s$) or passband. Apodization tries to avoid, or at least significantly reduce, any lateral symmetry in a resonator device, or at least in the active region thereof, to partially smooth out the spurious modes below $f_s$. An apodized shape is closer to a mode continuum or at least has an increased number of modes with dense spacing and smaller coupling than in a rectangle.

Figure 6A:
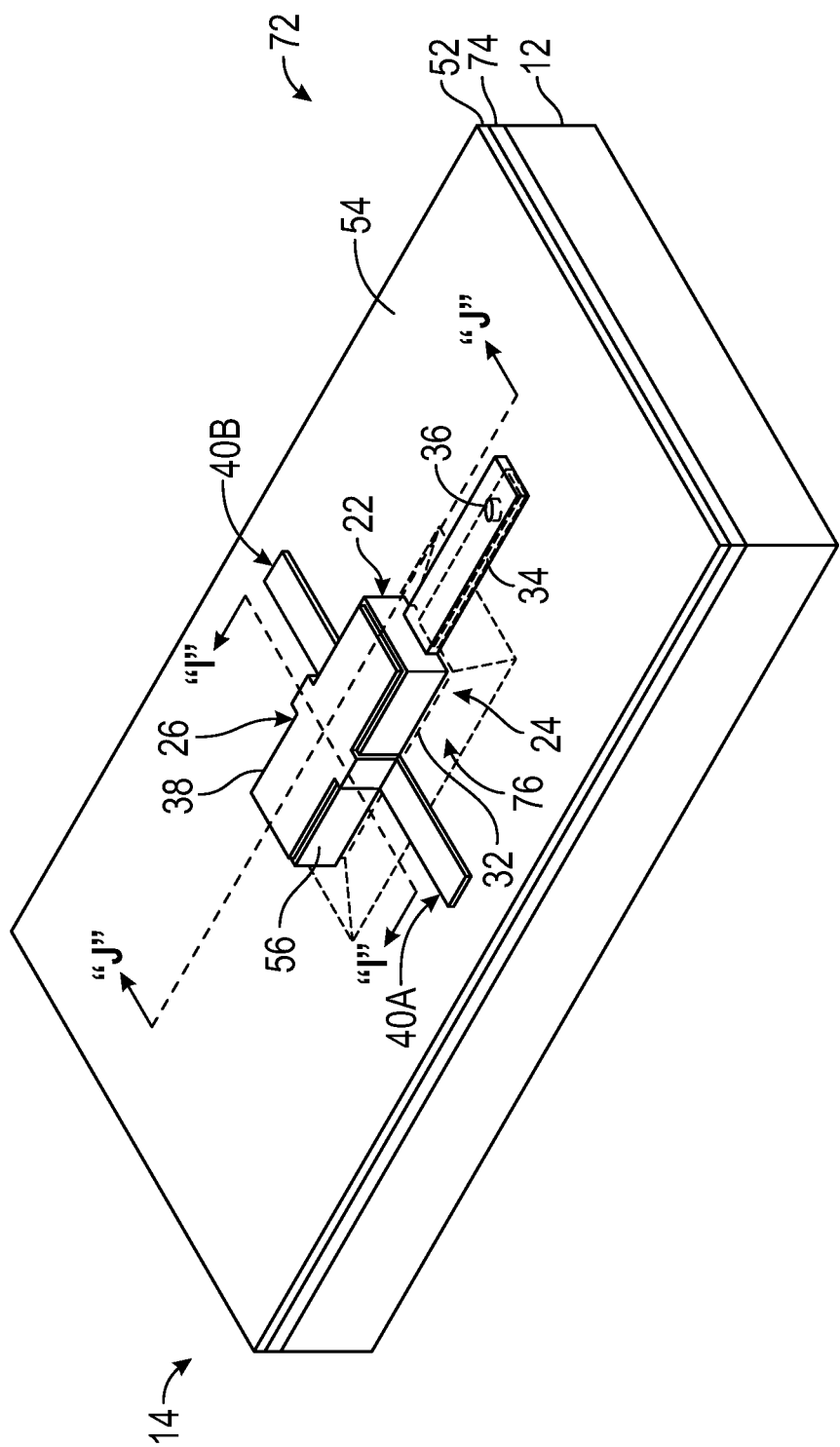
FIG. 6A is a schematic upper perspective view of at least a portion of a FBAR-type BAW resonator device according to another embodiment, with the BAW resonator device including a rectangular active region arranged over a support layer spanning a cavity in a substrate, with the active region including a piezoelectric material and being laterally surrounded by an inactive region that is devoid of (i.e., includes zero thickness of) piezoelectric material, thereby providing a discontinuity along opposing lateral edges of the piezoelectric material of the active region to reduce mechanical clamping of the active region in a direction of maximum lateral displacement in shear mode operation.

Although various preceding figures illustrate various solidly mounted resonator (SMR) type bulk acoustic wave MEMS resonator devices, it is to be appreciated that film bulk acoustic wave resonator (FBAR) devices may be employed in fluidic devices according to certain embodiments. FIGS. 6A-6C illustrate a FBAR-type BAW resonator device 72 incorporating a resonator structure 14 that includes a mesa-type rectangular active region 28 arranged over a support layer 74 spanning a cavity 76 defined in a substrate 12. The active region 28 includes a piezoelectric material 22 and an active region boundary 44, and is laterally surrounded by an inactive region 42 that is devoid of (i.e., includes zero thickness of) piezoelectric material 22, thereby providing a discontinuity along opposing lateral edges of the piezoelectric material 22 of the active region 28 to reduce mechanical clamping of the active region 28 in a direction of maximum lateral displacement in shear mode operation. As shown, the resonator device 72 is similar to that of FIGS. 2A-2C, except that the BAW resonator device 72 is an FBAR-type resonator instead of a solidly mounted resonator, and therefore does not include an acoustic reflector.

The resonator device 72 includes the substrate 12 (e.g., silicon or another semiconductor material) which defines a cavity 76 (e.g., trapezoidal cavity) covered by the support layer 74 (e.g., silicon dioxide), and includes the active region 28 registered with the cavity 76, with a portion of the piezoelectric material 22 being arranged between portions of a bottom side electrode 24 and a top side electrode 26. It is noted that the cavity 76 is trapezoidal in shape, with a base of the trapezoid arranged at the bottom surface of the substrate 12. It is noted that the resonator device 72 could be manufactured such that the base of the cavity 76 is at the top surface of the substrate 12 and extends at least partially (or fully) downward through the substrate 12. Further, in other embodiments, the cavity 76 may be provided in any suitable shape.

The bottom side electrode 24 is arranged over a portion of the support layer 74. The bottom side electrode 24 and the support layer 74 are overlaid with the piezoelectric material 22 (e.g., embodying inclined c-axis hexagonal crystal structure piezoelectric material such as AlN or ZnO), and the top side electrode 26 is arranged over at least a portion of a top surface of the piezoelectric material 22. The piezoelectric material 22 includes a c-axis 30 having an orientation distribution that is predominantly non-parallel to normal of a face of the substrate 12. The bottom side electrode 24 comprises an active segment 32, a trace 34, and an electrically conductive via 36, and the top side electrode includes an active central portion 38. Left and right electrical traces 40A, 40B including vertical portions 48A, 48B and horizontal portions 50A, 50B, respectively, are in conductive electrical communication with the active central portion 38. A portion of the piezoelectric material 22 arranged between the top side electrode 26 and the bottom side electrode 24 embodies the active region 28 of the resonator device 72. The active region 28 is arranged over and registered with the cavity 76 disposed below the support layer 74. The cavity 76 serves to confine acoustic waves induced in the active region 28 by preventing dissipation of acoustic energy into the substrate 12, since acoustic waves do not efficiently propagate across the cavity 76. In this respect, the cavity 76 provides an alternative to the acoustic reflectors 16 illustrated and described in connection with FIGS. 1A-5. Although FIGS. 6A-6C illustrate the cavity 76 as extending through an entire thickness of the substrate 12, in alternative embodiments, the cavity 76 may be bounded from above or below by a thinned portion of the substrate 12. Steps for forming the resonator device 72 may include depositing the support layer 74 over the substrate 12, defining the cavity 76 in the substrate 12, filling the cavity 76 with a sacrificial material (not shown) to provide support, optionally followed by planarization of the sacrificial material, removing the sacrificial material (e.g., using an etchant supplied through lateral edges of the substrate 12 or vertical openings defined in the substrate 12 or the support layer 74), depositing the bottom side electrode 24 over the support layer 74, growing (e.g., via sputtering or other appropriate methods) the piezoelectric material 22, and depositing the top side electrode 26.

To prevent electrical contact between the top side electrode 26 and the bottom side electrode 24, an electrically insulating barrier layer 52 (e.g., aluminum oxide [$Al_2O_3$]) is provided. The barrier layer 52 includes a vertical portion 54 and a horizontal portion 56, and is arranged generally below portions of the top side electrode 26, except under an active central portion 38 of the top side electrode 26 coinciding with the active region 28. The vertical portion 54 of the barrier layer 52 extends around at least a portion of the lateral surface of the active region 28, and extends upward to at least a height of the lateral surface of the active region 28. The horizontal portion 56 of the barrier layer 52 is positioned to cover at least a portion of the support layer 74.

In certain embodiments, as explained in more detail hereinafter, one or more BAW resonator structures with reduced mechanical clamping of an active region for enhanced shear mode response may be incorporated as part of a sensor suitable for operation with liquid samples or in liquid environments. The BAW MEMS resonator devices described previously herein lack any layers (e.g., including functionalization material) overlying active regions thereof that would permit such devices to be used as biochemical sensors. If desired, at least portions of a bulk acoustic wave MEMS resonator device as disclosed herein may be overlaid with various layers.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with an active region of the BAW resonator structure), such as: a hermeticity layer (e.g., to protect a top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

Figure 7:
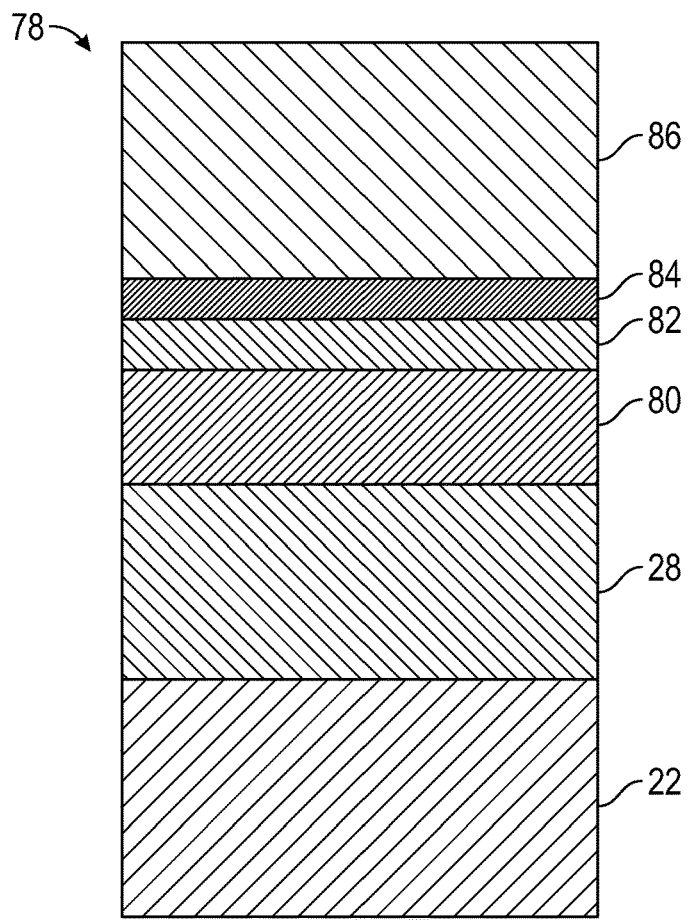
FIG. 7 is a schematic cross-sectional view of an upper portion of a MEMS BAW resonator device according to one embodiment of the present disclosure, including a top side electrode overlaid with a hermeticity layer, an interface layer, a self-assembled monolayer, and a functionalization (e.g., specific binding) material.

An example of a bulk acoustic wave MEMS resonator device overlaid with multiple layers to provide biosensing utility, and useable with fluidic devices according to certain embodiments, is provided in FIG. 7. FIG. 7 is a schematic cross-sectional view of an upper portion 78 of a BAW resonator device including a piezoelectric material 22 and a top side electrode 28 that is overlaid with a hermeticity layer 80, an interface layer 82, a self-assembled monolayer (SAM) 84, and a functionalization (e.g., specific binding or non-specific binding) material 86. In certain embodiments, one or more blocking materials (not shown) may be applied during fabrication, such as over portions of the interface layer 82 to prevent localized attachment of one or more subsequently deposited layers, or (if applied over selected regions of the SAM 84 or functionalization material 86) to prevent analyte capture in regions not overlying the active region of a BAW MEMS resonator device. Further disclosure regarding hermeticity layers, interface layers, self-assembled monolayers, and functionalization materials is set out below.

In certain embodiments, photolithography may be used to promote patterning of one or more layers (e.g., interface material or blocking material) over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 g/m$^2$/day). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 $g/m^2/day$) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a backbone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active regions of a multi-resonator structure (i.e., one or more resonator structures including multiple active regions), optionally in combination with one or more active regions that are devoid of specific binding materials to serve as comparison (or "reference") regions. In certain embodiments, a functionalization (e.g., bio-functionalization) material may provide non-specific binding utility.

Certain embodiments are directed to a fluidic device including a BAW resonator device as disclosed herein and including a fluidic passage (e.g., channel) arranged to conduct a liquid to contact at least one functionalization (e.g., specific binding) material. Such a device may be microfluidic in scale, and comprise at least one microfluidic channel (e.g., having at least one dimension, such as height and/or width, of no greater than about 500 microns, or about 250 microns, or about 100 microns). For example, following fabrication of a bulk acoustic wave MEMS resonator device and deposition of an interface layer and a SAM over portions thereof (optionally preceded by deposition of a hermeticity layer), a microfluidic device may be fabricated by forming one or more walls defining lateral boundaries of a microfluidic channel preferably containing the active region of at least one acoustic resonator, followed by application of a cover or cap layer to enclose the microfluidic channel. In certain embodiments, functionalization (e.g., specific binding) material may be applied after formation of walls of a microfluidic channel, but prior to application of the cover or cap layer. Walls of a microfluidic channel may be formed of any suitable material, such as SU-8 negative epoxy resist, other photoresist material, or laser-cut "stencil" layers of thin polymeric materials and/or laminates, optionally including one or more self-adhesive surfaces (e.g., adhesive tape). In certain embodiments, a cover or cap layer may be integrally formed with one or more walls (e.g., via molding or another suitable process) to define upper and lateral boundaries of at least one microfluidic channel, and the integrally formed cover/wall structure may be applied (e.g., adhered or otherwise bonded) over at least a portion of a bulk acoustic wave resonator structure to enclose the at least one microfluidic channel.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. An ideal blocking buffer would bind to all potential sites of nonspecific interaction away from an active region. To optimize a blocking buffer for a particular analysis, empirical testing may be used to determine signal-to-noise ratio. No single chemical blocking material is ideal for every situation, since each antibody-antigen pair has unique characteristics.

Figure 8:
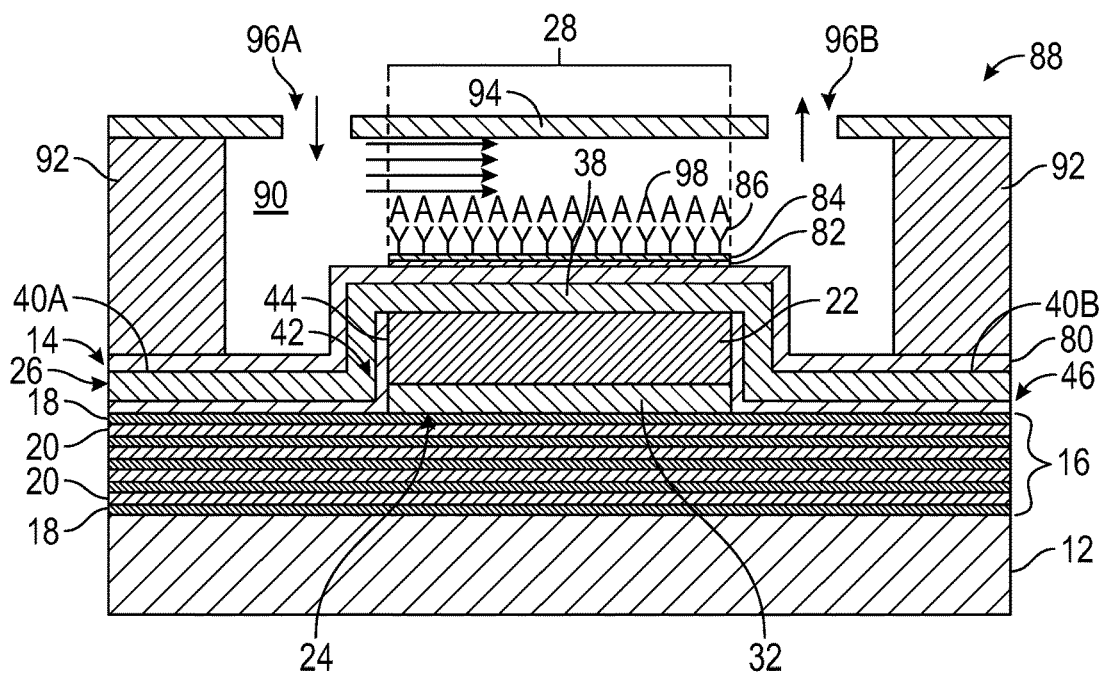
FIG. 8 is a schematic cross-sectional view of a portion of a fluidic device (e.g., a biochemical sensor device) including a microfluidic channel bounded from below by a solidly mounted BAW resonator device overlaid with functionalization material, bounded laterally by walls, and bounded from above by a cover or cap layer defining fluidic ports, according to one embodiment of the present disclosure.

FIG. 8 is a schematic cross-sectional view of a portion of a fluidic device 88 (e.g., a biochemical sensor device) including a microfluidic channel 90 bounded from below by a BAW resonator device 46 incorporating a resonator structure 14 (as shown in FIGS. 2A-2C, although any BAW resonator structure disclosed herein may be used), bounded laterally by walls 92, and bounded from above by a cover or cap layer 94 defining upper or top surface fluidic ports 96A, 96B. The fluidic device 88 includes a substrate 12 overlaid with an acoustic reflector 16 (including alternating low acoustic impedance and high acoustic impedance layers 18, 20), and a bottom side electrode 24 (including an active segment 32) arranged generally below a piezoelectric material 22. A top side electrode 26 (including an active central portion 38, and left and right traces 40A, 40B) extends over a portion of the piezoelectric material 22, wherein a portion of the piezoelectric material 22 arranged between the top side electrode 26 and the bottom side electrode 24 embodies an active region 28 of the BAW resonator device 46. The active region 28 is surrounded by an inactive region 42, with an active region boundary 44 arranged therebetween. The top side electrode 26 and the piezoelectric material 22 are overlaid with a hermeticity layer 80, an interface layer 82, and a self-assembled monolayer (SAM) 84. Optionally, portions of the SAM 84 extending away from the active region 28 could be overlaid with a chemical or biological blocking material (not shown) to prevent attachment of specific binding material. A portion of the SAM 84 registered with the active region 28 is overlaid with functionalization (e.g., specific binding) material 86 arranged to bind a specified analyte 98.

Walls 92 that are laterally displaced from the active region 28 extend upward from the hermeticity layer 80 to define lateral boundaries of the microfluidic channel 90 containing the active region 28. Such walls 92 may be formed of any suitable material, such as a laser-cut "stencil" layer of thin polymeric materials and/or laminate materials, optionally including one or more self-adhesive surfaces (e.g. adhesive tape). Optionally such walls 92 may be formed prior to deposition of the SAM 84, functionalization material 86, and chemical or biological blocking material with an SU-8 negative epoxy resist or other photoresist material. The cover or cap layer 94 defining fluidic ports 96A, 96B is further provided to provide an upper boundary for the microfluidic channel 90. The cover or cap layer 94 may be formed by defining ports 96A, 96B (e.g., via laser cutting or water jet cutting) in a layer of an appropriate material (e.g., a substantially inert polymer, glass, silicon, ceramic, or the like), and adhering the cover or cap layer 94 to top surfaces of the walls 92.

In use of the fluidic device 88, a fluid sample may be supplied through the first fluidic port 96A, into the microfluidic channel 90 over the active region 28, and through the second fluidic port 96B to exit the microfluidic channel 90. As shown in FIG. 8, the analyte 98 supplied by the fluid sample is bound to the functionalization (e.g., specific binding) material 86. When a bulk acoustic wave is induced in the active region 28 by supplying an electrical (e.g., alternating current) signal to the bottom and top side electrodes 24, 26, detection of a change in at least one of a frequency property, an amplitude magnitude property, or a phase property of the bulk acoustic wave resonator structure indicates a presence and/or quantity of target species (i.e., analyte) bound to the functionalization material 86.

Those skilled in the art will recognize improvements and modifications to the preferred embodiments of the present disclosure. All such improvements and modifications are considered within the scope of the concepts disclosed herein and the claims that follow.

What is claimed is:

1. A micro-electrical-mechanical system (MEMS) resonator device comprising:
   a substrate; and
   a bulk acoustic wave resonator structure arranged over at least a portion of the substrate, the bulk acoustic wave resonator structure including a piezoelectric material comprising a c-axis having an orientation distribution that is predominantly non-parallel to normal of a face of the substrate, a top side electrode arranged over the piezoelectric material, and a bottom side electrode arranged between the piezoelectric material and the substrate, wherein at least a portion of the piezoelectric material is arranged between the top side electrode and the bottom side electrode to form an active region;

wherein the active region is laterally surrounded by an inactive region, and a thickness of piezoelectric material of at least a portion of the inactive region is less than a thickness of piezoelectric material of the active region, such that at least an upper portion of the inactive region along a boundary of the active region is devoid of piezoelectric material, defining at least one discontinuity along at least upper portions of opposing lateral edges of piezoelectric material of the active region, wherein the at least one discontinuity is configured to reduce mechanical clamping of the active region in a direction of maximum lateral displacement in shear mode operation of the bulk acoustic wave resonator structure; wherein the active region comprises a length parallel to the direction of maximum lateral displacement in shear mode operation of the bulk acoustic wave resonator structure, and the active region comprises a width perpendicular to the length, wherein the length extends between a first lengthwise end and a second lengthwise end of the active region; and wherein the length is greater than the width.

2. The MEMS resonator device of claim 1, wherein:
the at least a portion of the piezoelectric material arranged between the top side electrode and the bottom side electrode comprises a nominal thickness; and
at least a portion of a lateral perimeter of the active region is bounded by a reduced thickness portion of the piezoelectric material having a thickness in a range of from 0% to about 50% of the nominal thickness.

3. The MEMS resonator device of claim 1, wherein:
the at least one discontinuity is bounded at least in part by the first lengthwise end and the second lengthwise end.

4. The MEMS resonator device of claim 1, wherein the at least one discontinuity surrounds at least about 60% of a perimeter of the active region.

5. The MEMS resonator device of claim 1, wherein the bulk acoustic wave resonator structure comprises an acoustic reflector structure arranged between the substrate and the bottom side electrode.

6. The MEMS resonator device of claim 1, wherein the substrate defines a recess, and a support layer is arranged between the recess and the bulk acoustic wave resonator structure.

7. The MEMS resonator device of claim 1, wherein a hermeticity layer is arranged over at least a portion of at least one of: the top side electrode, the bottom side electrode, or at least one lateral edge of the active region.

8. The MEMS resonator device of claim 1, wherein:
the piezoelectric material comprises at least one anchor portion extending in a direction perpendicular to the length of the active region, and contacting the active region midway between lengthwise ends of the active region.

9. The MEMS resonator device of claim 8, wherein at least a portion of at least one of the top side electrode or the bottom side electrode extends along the at least one anchor portion of the piezoelectric material.

10. The MEMS resonator device of claim 1, further comprising a dielectric material arranged over lateral edges of the active region.

11. A fluidic device comprising:
the MEMS resonator device of claim 1;
at least one functionalization material arranged over at least a portion of the active region; and
a fluidic channel containing the active region.

12. A method for biological or chemical sensing, the method comprising:
supplying a fluid containing a target species into the fluidic channel of the fluidic device of claim 11, wherein said supplying is configured to cause at least some of the target species to bind to the at least one functionalization material;
inducing a bulk acoustic wave in the active region; and
sensing a change in at least one of a frequency property, an amplitude magnitude property, or a phase property of the bulk acoustic wave resonator structure to indicate at least one of presence or quantity of target species bound to the at least one functionalization material.

13. The fluidic device of claim 11, wherein the at least one functionalization material comprises at least one of a specific binding material or a non-specific binding material.

14. The fluidic device of claim 11, further comprising a self-assembled monolayer arranged between the at least one functionalization material and the top side electrode.

15. The fluidic device of claim 14, further comprising an interface layer arranged between the top side electrode and the self-assembled monolayer.

16. A method for fabricating a micro-electrical-mechanical system (MEMS) resonator device, the method comprising:
forming a base structure including a substrate, a piezoelectric material arranged over at least a portion of the substrate and comprising a c-axis having an orientation distribution that is predominantly non-parallel to normal of a face of the substrate, and a bottom side electrode arranged between the substrate and at least a portion of the piezoelectric material, wherein the piezoelectric material comprises a nominal thickness;
removing a portion of the piezoelectric material to define a reduced thickness portion of the piezoelectric material having a thickness in a range of from 0% to about 50% of the nominal thickness;
forming a top side electrode over a portion of the piezoelectric material, wherein at least a portion of the piezoelectric material comprising the nominal thickness is arranged between the top side electrode and the bottom side electrode to form an active region of a bulk acoustic wave resonator structure; and
depositing a hermeticity layer over at least a portion of at least one of: the top side electrode, the bottom side electrode, or at least one lateral edge of the active region,
wherein at least a portion of a lateral perimeter of the active region is bounded by the reduced thickness portion of the piezoelectric material, defining at least one discontinuity configured to reduce mechanical clamping of the active region in a direction of maximum lateral displacement in shear mode operation of the bulk acoustic wave resonator structure.

17. The method of claim 16, further comprising forming a self-assembled monolayer over at least a portion of the top side electrode, and applying at least one functionalization material over at least a portion of the self-assembled monolayer, wherein at least a portion of the at least one functionalization material is registered with the active region.

18. A micro-electrical-mechanical system (MEMS) resonator device comprising:
   a substrate; and
   a bulk acoustic wave resonator structure arranged over at least a portion of the substrate, the bulk acoustic wave resonator structure including a piezoelectric material comprising a c-axis having an orientation distribution that is predominantly non-parallel to normal of a face of the substrate, a top side electrode arranged over the piezoelectric material, and a bottom side electrode arranged between the piezoelectric material and the substrate, wherein at least a portion of the piezoelectric material is arranged between the top side electrode and the bottom side electrode to form an active region;
   wherein the active region is laterally surrounded by an inactive region, and a thickness of piezoelectric material of at least a portion of the inactive region is less than a thickness of piezoelectric material of the active region, such that at least an upper portion of the inactive region along a boundary of the active region is devoid of piezoelectric material, defining at least one discontinuity along at least upper portions of opposing lateral edges of piezoelectric material of the active region, wherein the at least one discontinuity is configured to reduce mechanical clamping of the active region in a direction of maximum lateral displacement in shear mode operation of the bulk acoustic wave resonator structure; wherein the active region comprises a length parallel to the direction of maximum lateral displacement in shear mode operation of the bulk acoustic wave resonator structure, and the active region comprises a width perpendicular to the length, wherein the piezoelectric material comprises at least one anchor portion extending in a direction perpendicular to the length of the active region and contacting the active region midway between lengthwise ends of the active region.

* * * * *